(12) United States Patent
Fukushima et al.

(10) Patent No.: US 10,444,249 B2
(45) Date of Patent: Oct. 15, 2019

(54) ION SENSOR

(71) Applicant: JAPAN SCIENCE AND TECHNOLOGY AGENCY, Kawaguchi-shi (JP)

(72) Inventors: Takanori Fukushima, Yokohama (JP); Fumitaka Ishiwari, Yokohama (JP); Hanako Hasebe, Yokohama (JP); Takao Someya, Bunkyo-ku (JP); Tsuyoshi Sekitani, Bunkyo-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 350 days.

(21) Appl. No.: 14/908,954

(22) PCT Filed: Apr. 11, 2014

(86) PCT No.: PCT/JP2014/060519
§ 371 (c)(1),
(2) Date: Jan. 29, 2016

(87) PCT Pub. No.: WO2015/015844
PCT Pub. Date: Feb. 5, 2015

(65) Prior Publication Data
US 2016/0169920 A1 Jun. 16, 2016

(30) Foreign Application Priority Data

Jul. 30, 2013 (JP) .................................. 2013-157754

(51) Int. Cl.
*G01N 33/00* (2006.01)
*G01N 33/84* (2006.01)
(Continued)

(52) U.S. Cl.
CPC .......... *G01N 33/84* (2013.01); *C07C 69/017* (2013.01); *C07C 69/54* (2013.01); *C07C 219/34* (2013.01);
(Continued)

(58) Field of Classification Search
CPC ...................................................... G01N 33/84
(Continued)

(56) References Cited

U.S. PATENT DOCUMENTS 5,128,419 A     7/1992   Fong et al.
5,298,583 A *   3/1994   Heiliger ............... G01N 33/533
                                                                        526/273
(Continued)

FOREIGN PATENT DOCUMENTS

CN     102617779 A     8/2012
JP      4-233918 A      8/1992
(Continued)

OTHER PUBLICATIONS

Tracy et al. "Enhanced Photoluminescence from Group 14 Metalloles in Aggregated and Solid Solutions" Inorg. Chem. 2005, 44, 2003-2011 (Year: 2005).*

(Continued)

*Primary Examiner* — Christine T Mui
*Assistant Examiner* — Emily R. Berkeley
(74) *Attorney, Agent, or Firm* — Oblon, McClelland, Maier & Neustadt, L.L.P.

(57) ABSTRACT

Provided is a compound including a repeating unit (A) having a carboxyl group on a side chain thereof and a repeating unit (B) having a carboxylate group having an ester residue exhibiting an aggregation-induced emission capability on a side chain thereof and the compound is useful (Continued)

as a polyvalent metal ion sensor such as calcium ions that is capable of reversible sensing and of being integrated into a device.

19 Claims, 20 Drawing Sheets

(51) Int. Cl.

| | |
|---|---|
| C08F 220/30 | (2006.01) |
| C08F 220/34 | (2006.01) |
| C07C 69/017 | (2006.01) |
| C07C 69/54 | (2006.01) |
| C07C 219/34 | (2006.01) |
| C08F 220/06 | (2006.01) |
| G01N 21/64 | (2006.01) |
| G01N 31/22 | (2006.01) |

(52) U.S. Cl.
CPC .......... *C08F 220/06* (2013.01); *C08F 220/30* (2013.01); *C08F 220/34* (2013.01); *G01N 21/6428* (2013.01); *G01N 31/22* (2013.01)

(58) Field of Classification Search
USPC .......................................................... 436/73
See application file for complete search history.

(56) References Cited

U.S. PATENT DOCUMENTS

| | | |
|---|---|---|
| 2006/0051872 A1 | 3/2006 | Sailor et al. |
| 2009/0137059 A1 | 5/2009 | Trogler et al. |
| 2009/0270279 A1 | 10/2009 | Serafinowski et al. |
| 2010/0298590 A1 | 11/2010 | Hayek et al. |
| 2013/0164531 A1 | 6/2013 | Natarajan et al. |

FOREIGN PATENT DOCUMENTS

| | | |
|---|---|---|
| JP | 2001-106734 A | 4/2001 |
| JP | 2002-268258 A | 9/2002 |
| JP | 2007-47518 A | 2/2007 |
| JP | 2007-238467 A | 9/2007 |
| JP | 2010-112777 A | 5/2010 |
| JP | 2011-180018 A | 9/2011 |

OTHER PUBLICATIONS

Luo et al. "Aggregation-induced emission of 1-methyl-1,2,3,4,5-pentaphenylsilole" Chem. Commun., 2001, 1740-1741 (Year: 2001).*
Partial Supplementary European Search Report dated Feb. 24, 2017 in Patent Application No. 14832272.0.
K. Edelmann, et al., "Copolymers from oligosiloxane methacrylates as a plasticizer-free membrane matrix for ion-selective sensors" Polymer, vol. 46, No. 2, XP002764364, 2005, pp. 407-417.
Grzegorz Grynkiewicz, et al., "A new Generation of Ca2+ Indicators with Greatly Improved Fluorescence Properties", The Journal of Biological Chemistry, Mar. 25, 1985, vol. 206, pp. 3440-3450 (11 pages).
International Search Report dated Jul. 15, 2014 for PCT/JP2014/060519 filed on Apr. 11, 2014.
Combined Office Action and Search Report dated May 2, 2017 in Chinese Patent Application No. 201480043534.0 with English translation of categories of cited documents.
Hanako Hasebe, et al., "Selective ion sensing by polyacrylic acid bearing aggregation-induced emissive fluorophore" Polymer Preprints, vol. 62, No. 1, 2013, 12 Pages (with English Abstract).

* cited by examiner

[Figure 1]
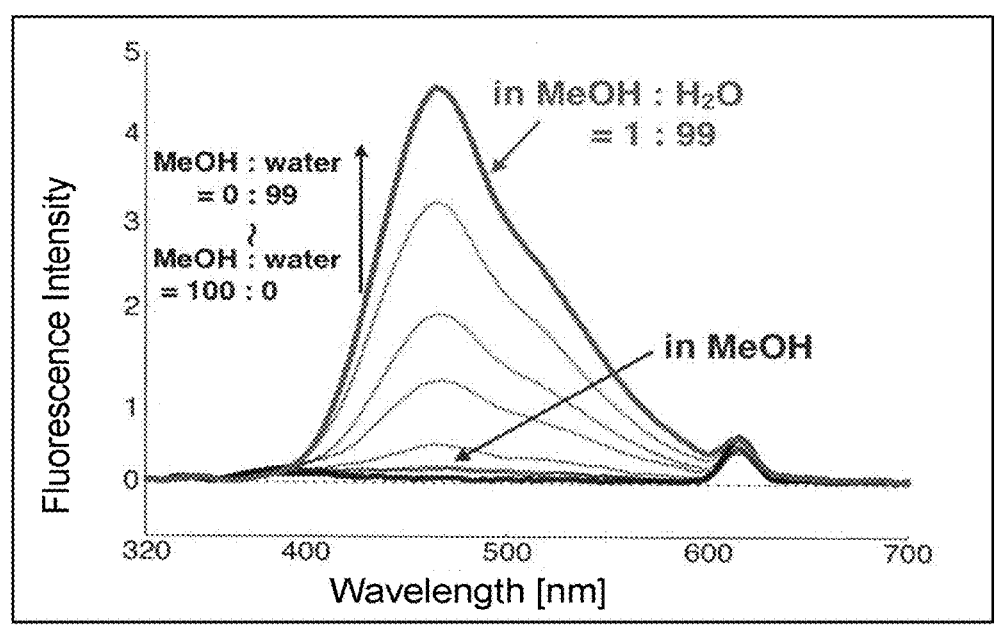

[Figure 2]
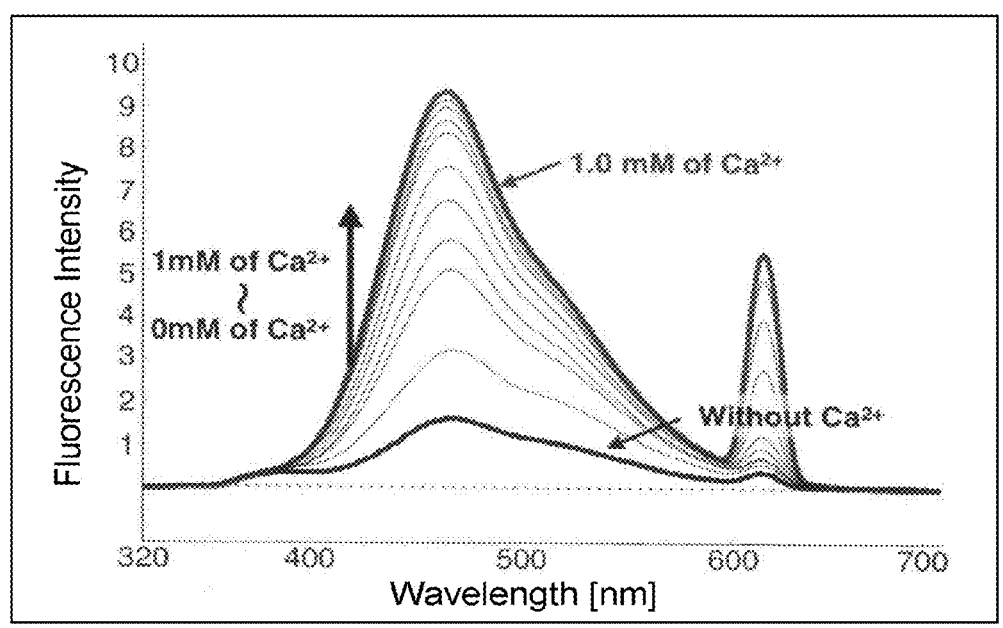

[Figure 3]
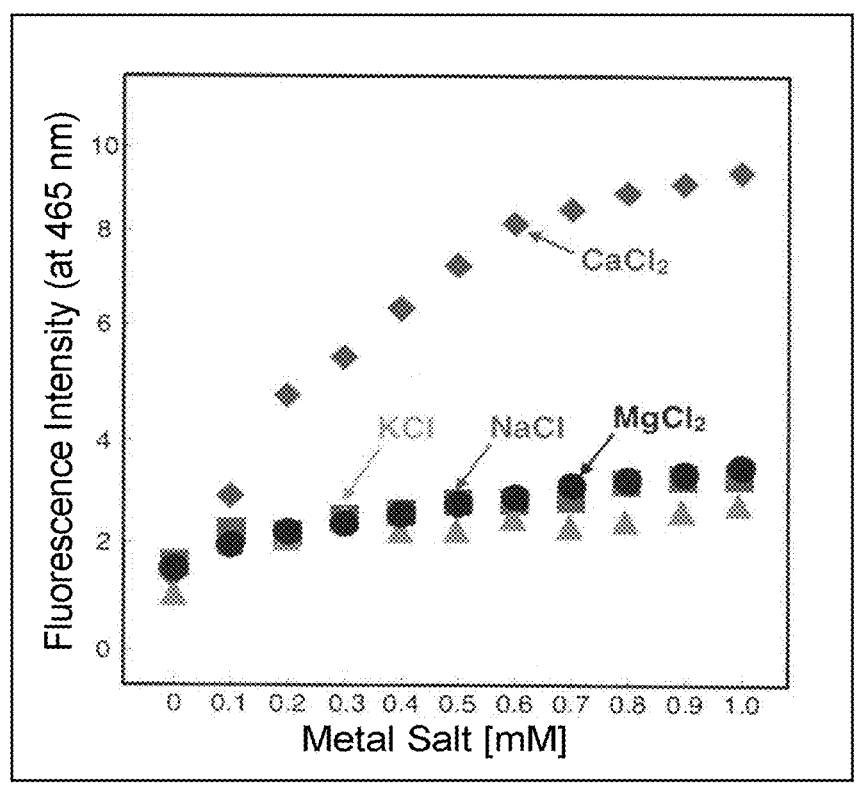

[Figure 4]
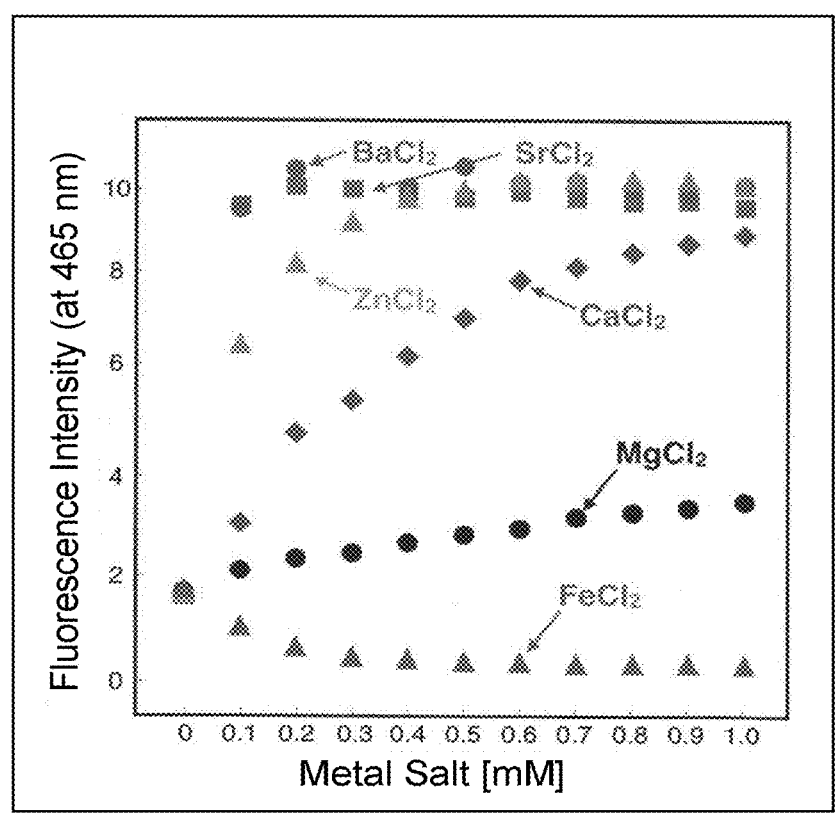

[Figure 5]
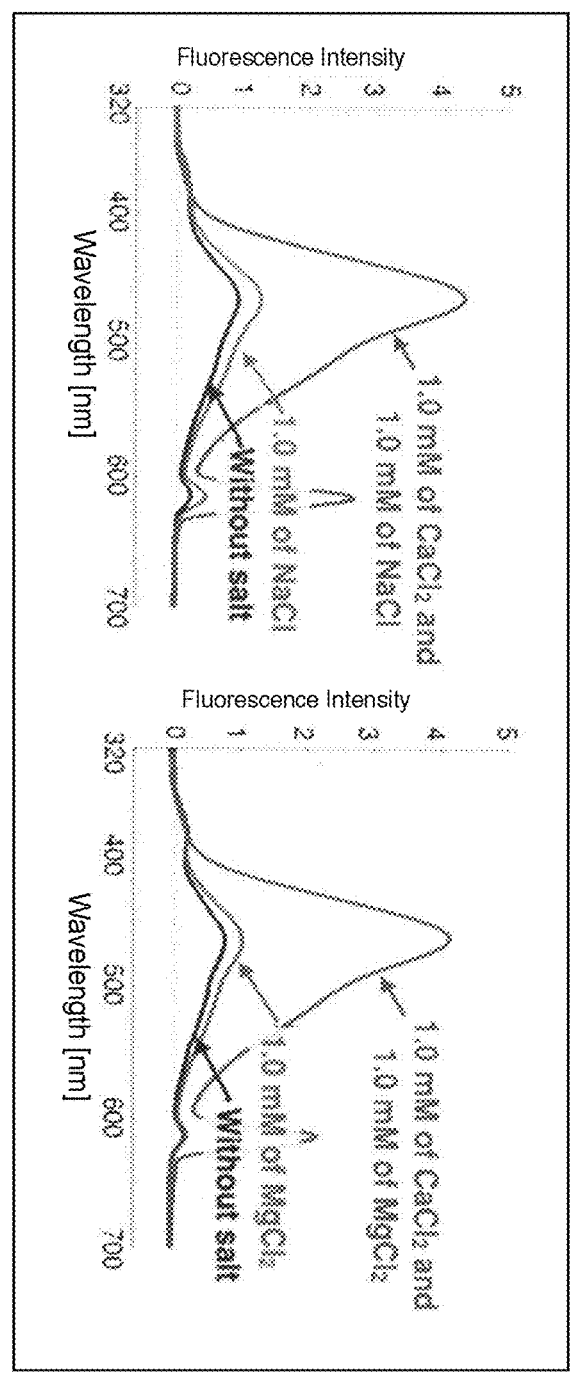

[Figure 6]
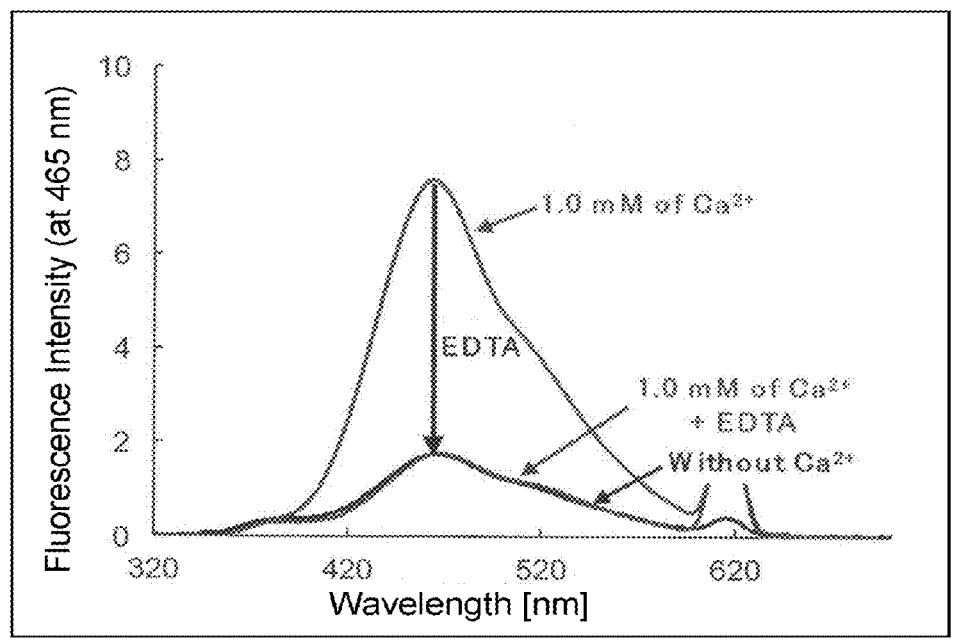

[Figure 7]
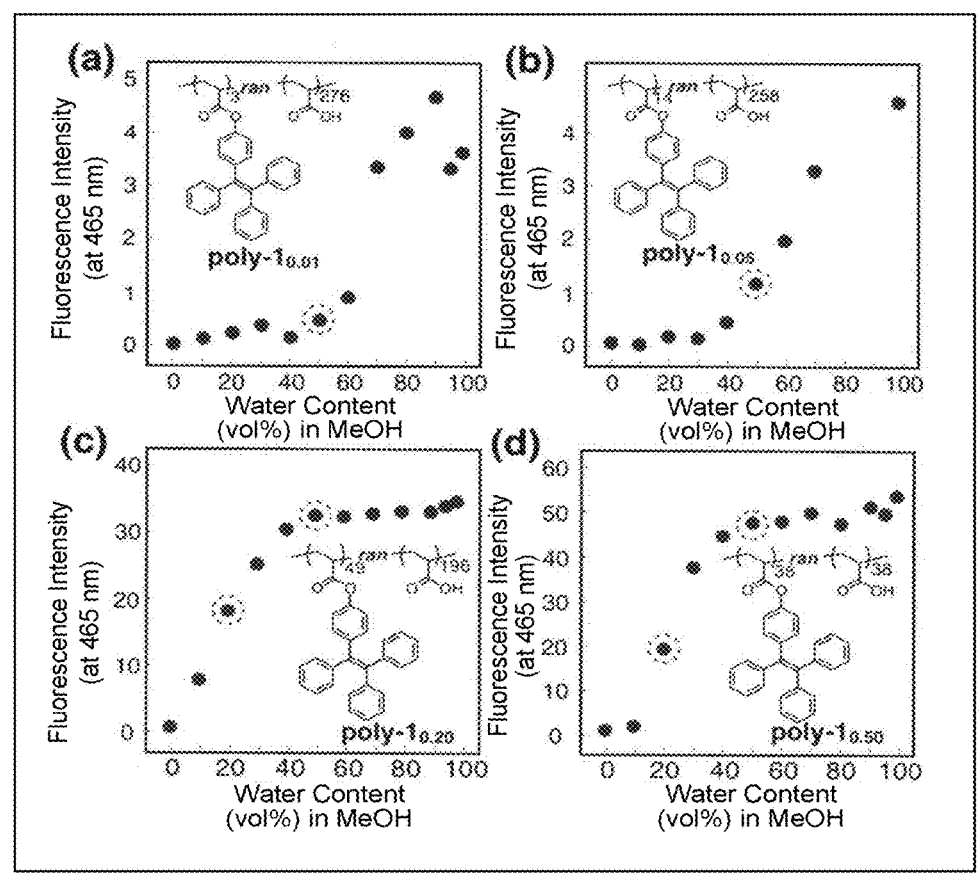

[Figure 8]
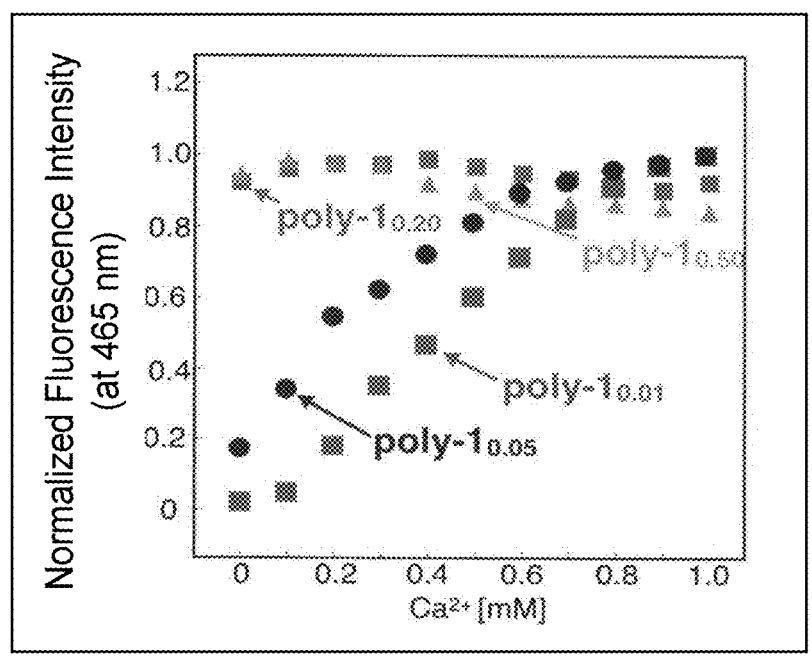

[Figure 9]
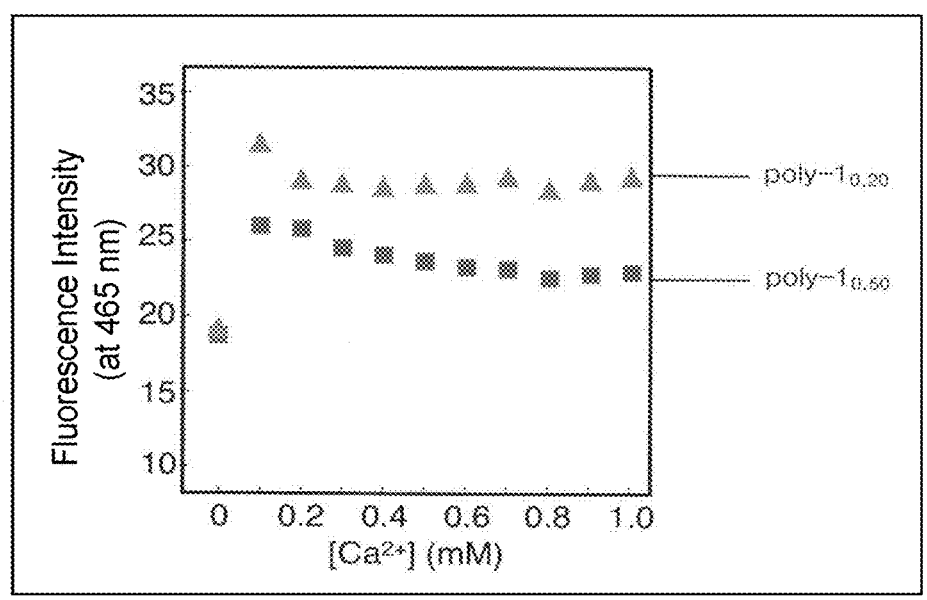

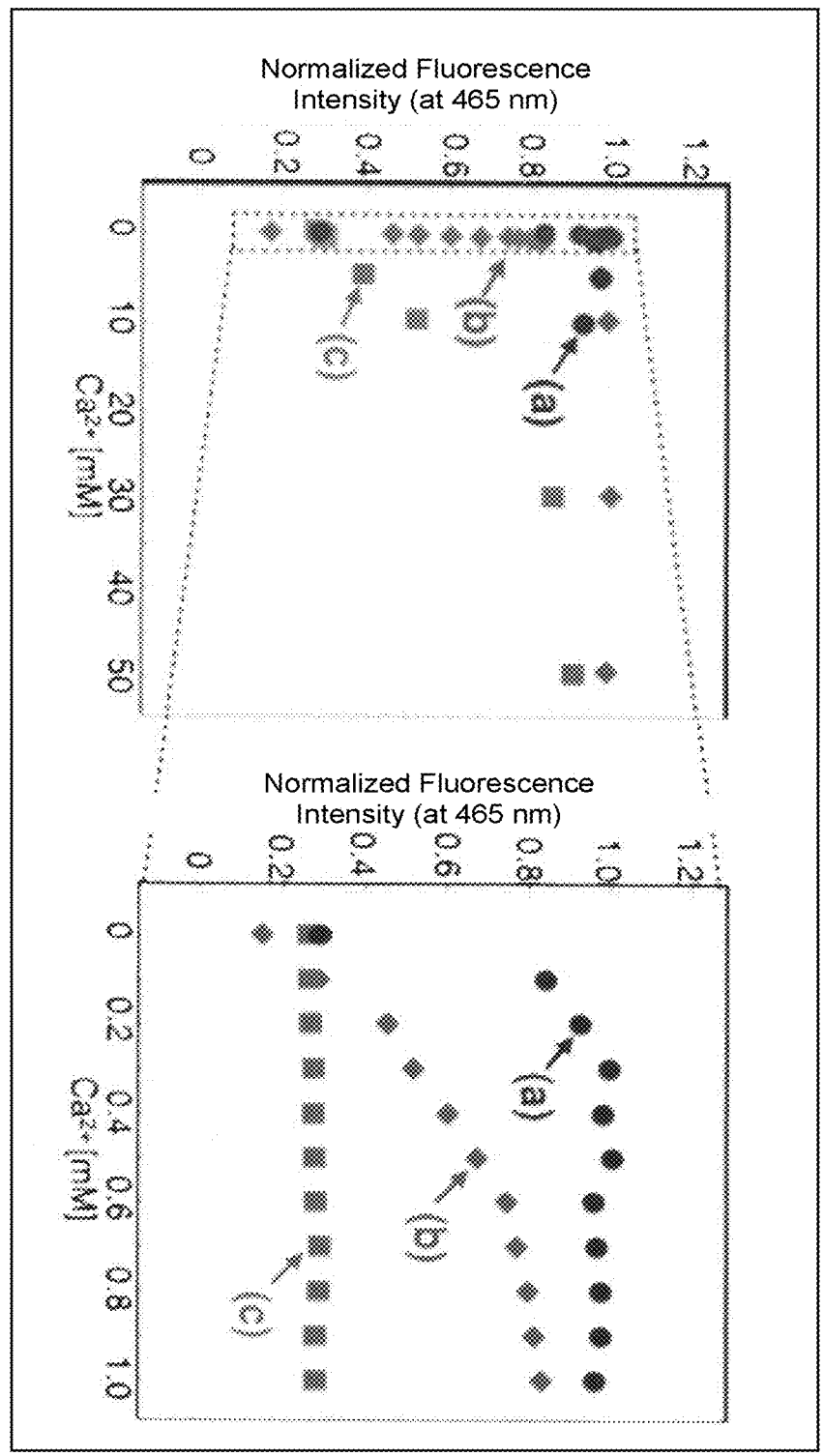
[Figure 10]

[Figure 11]
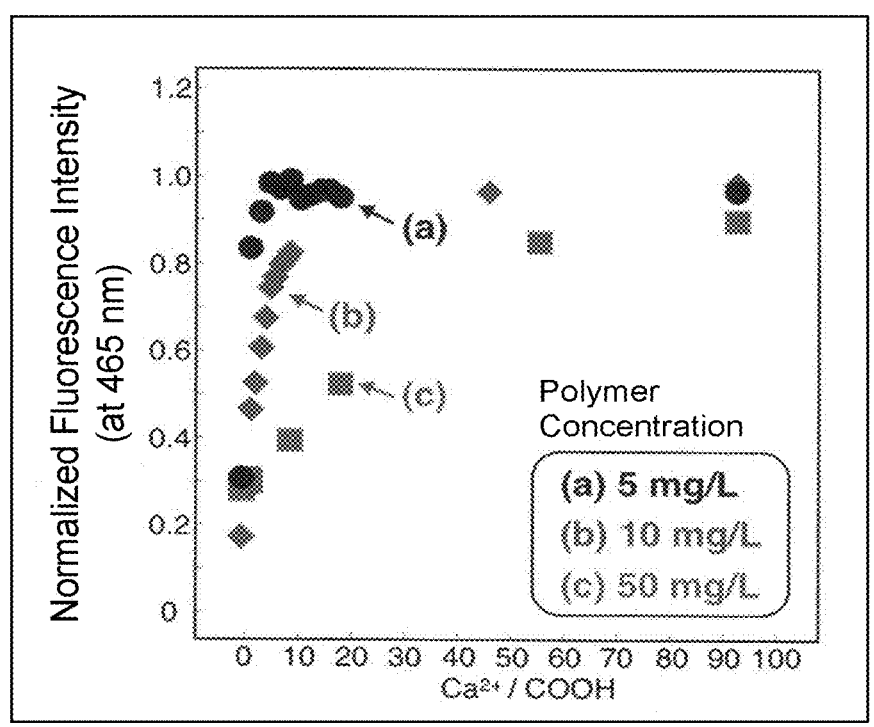

[Figure 12]
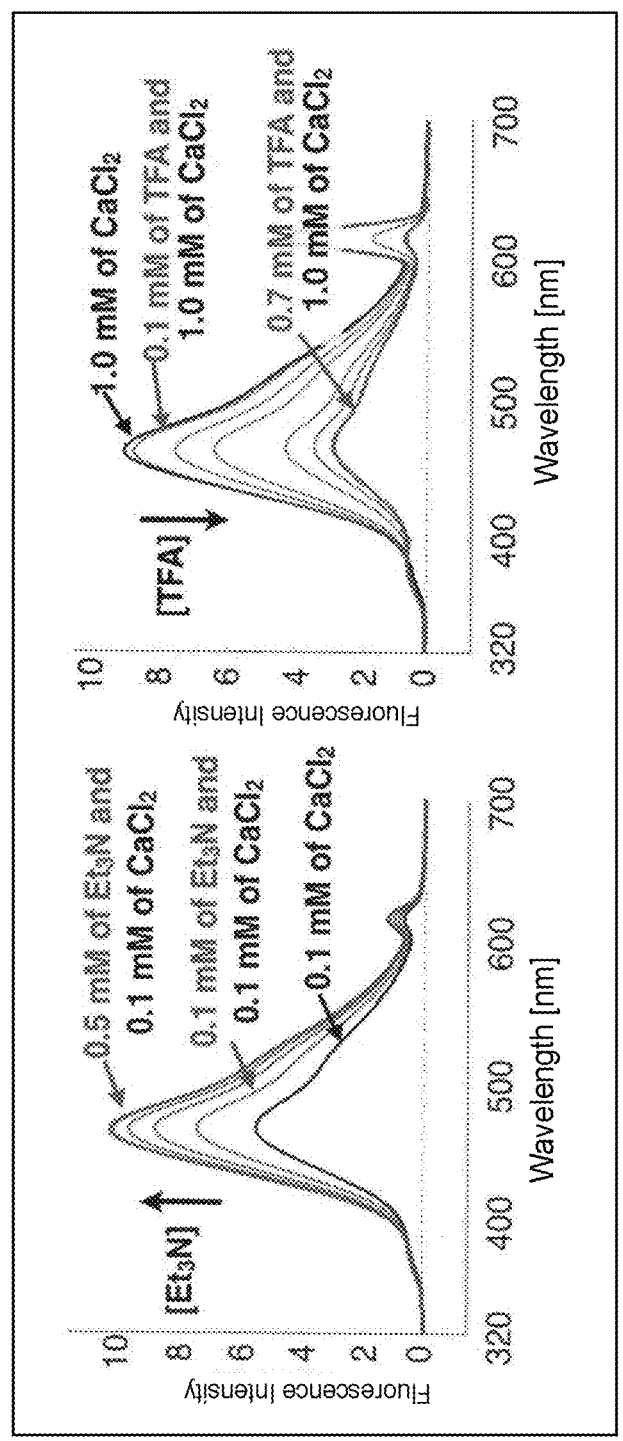

[Figure 13]
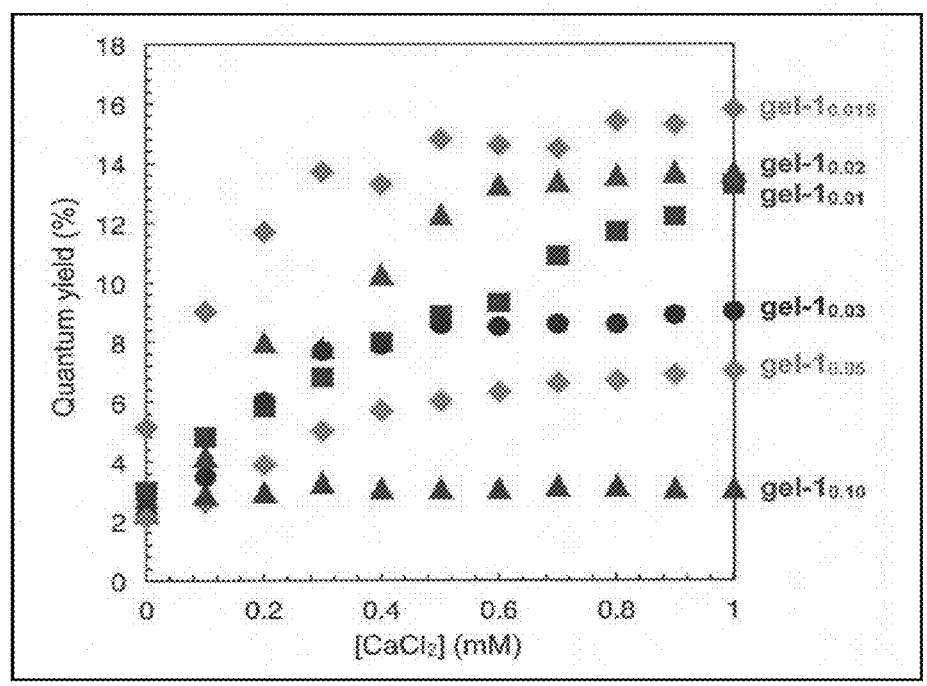

[Figure 14]
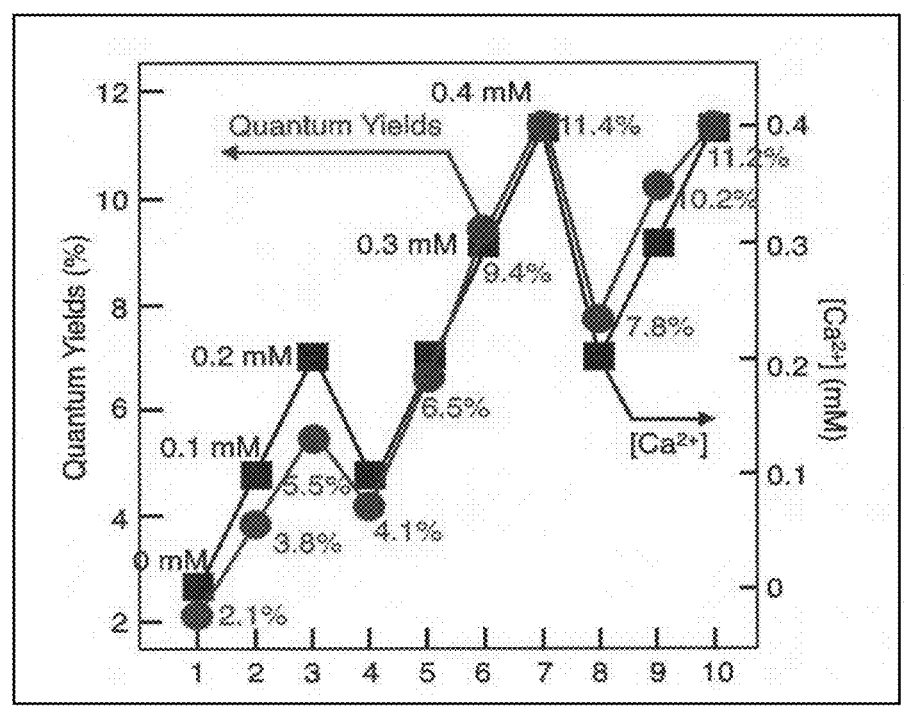

[Figure 15]
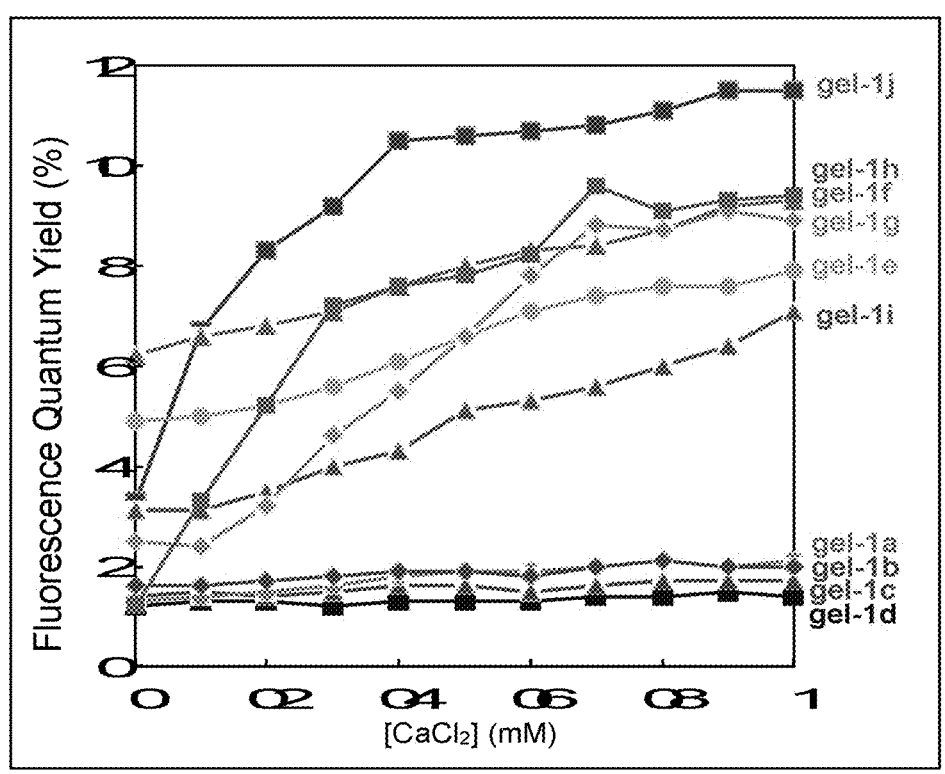

[Figure 16]
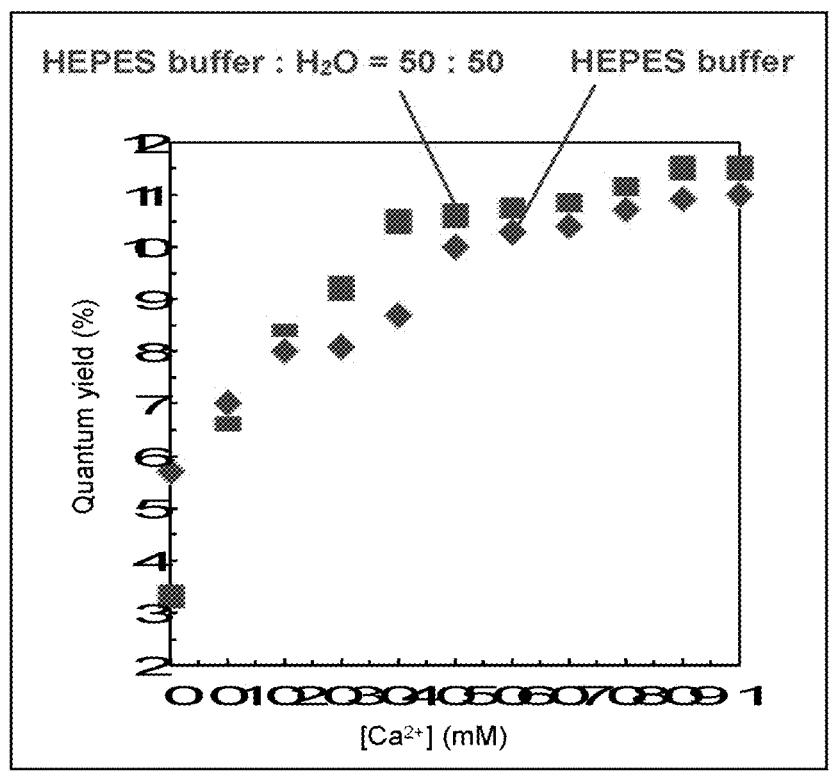

[Figure 17]
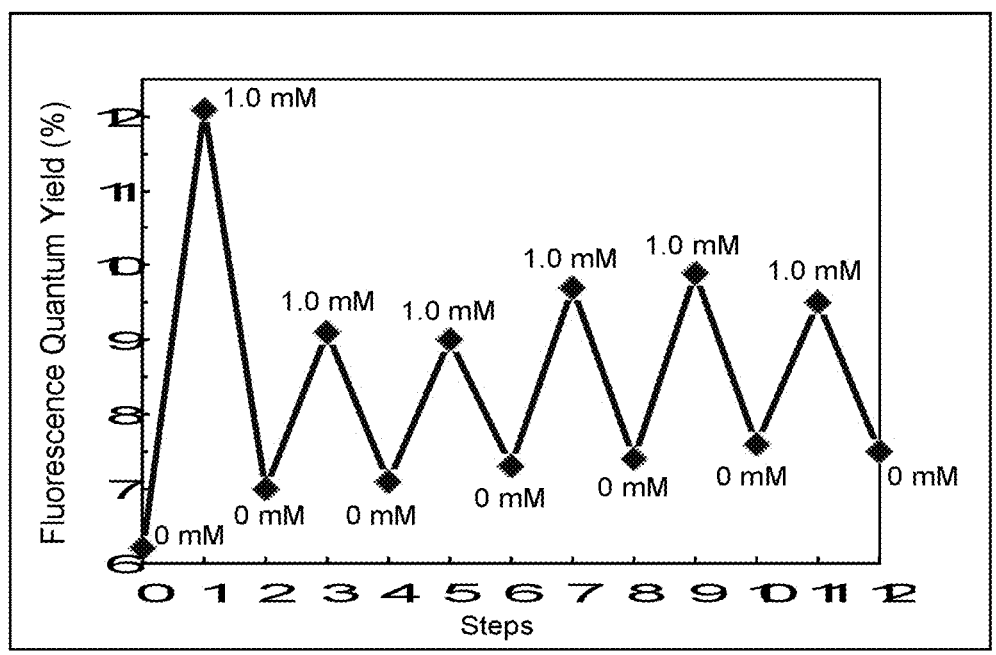

[Figure 18]
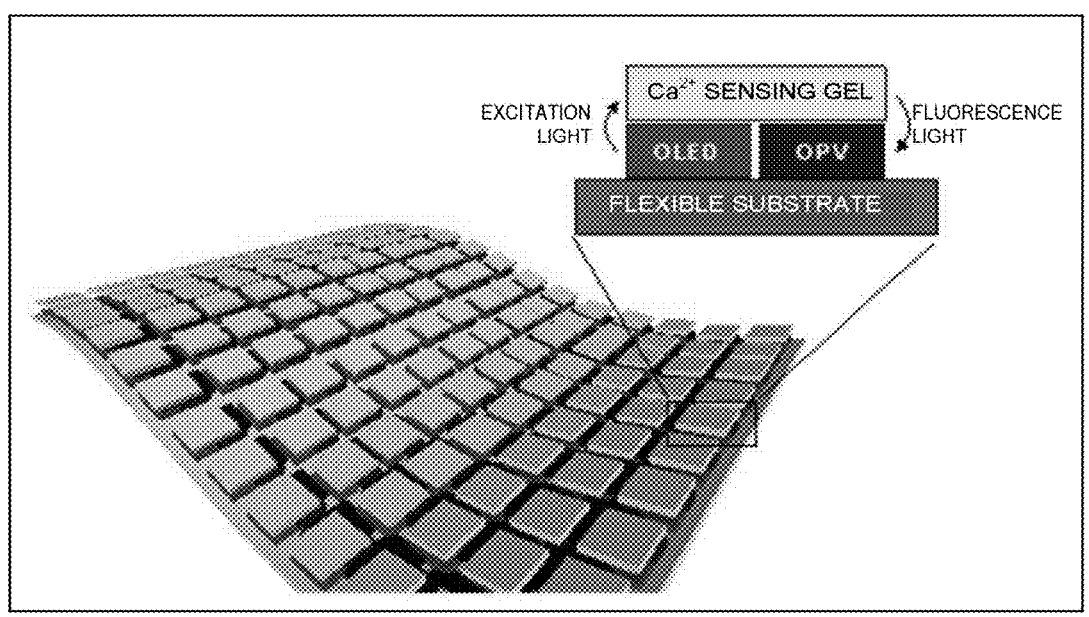

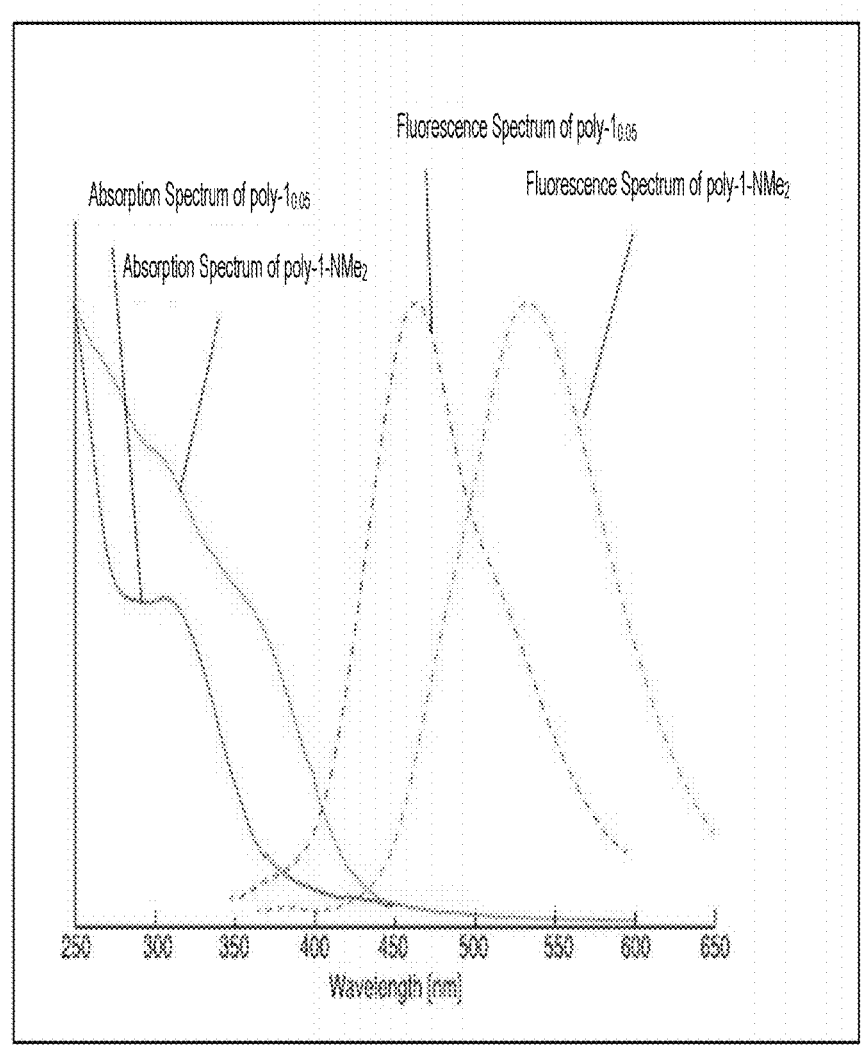
[Figure 19]

[Figure 20]
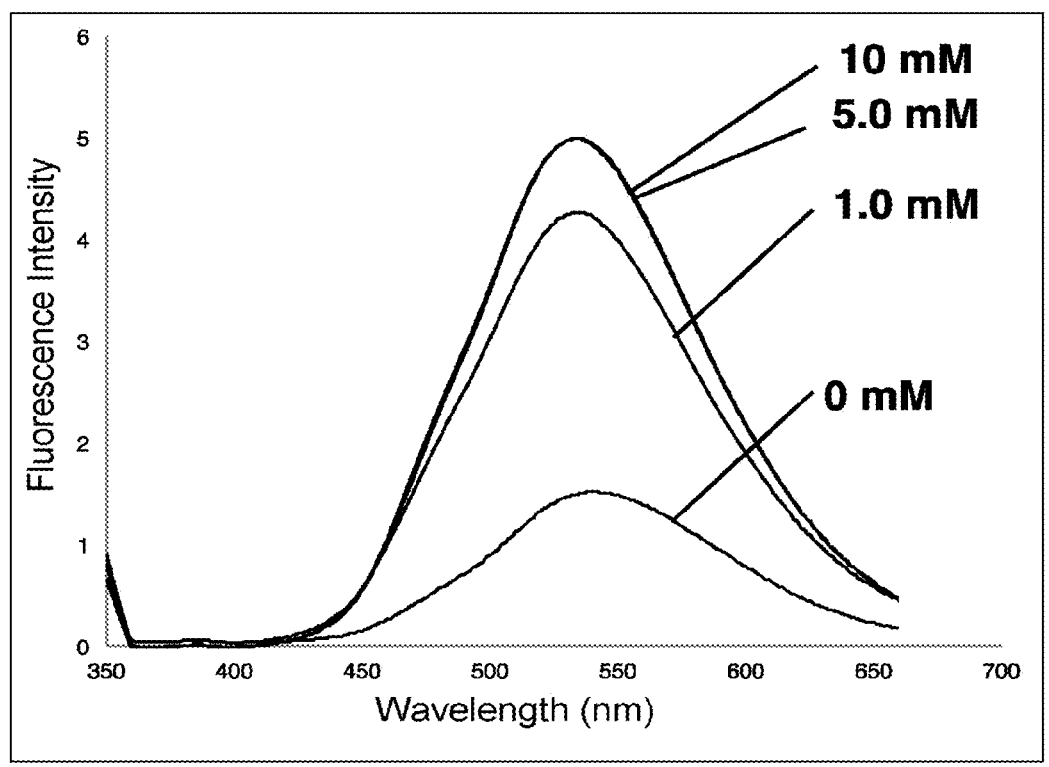

ION SENSOR

TECHNICAL FIELD

The present invention relates to a novel copolymer, and a device for detecting polyvalent metal ions using the copolymer.

BACKGROUND ART

Calcium exists in vivo as a component of bones, and it also causes important actions on contraction of muscles, excitation transmission of nerves, activation of enzymes, secretion of hormones, and the like. Specifically, calcium plays a role in the regulation of cell osmotic pressure, antagonism to Na or K ions, regulation of excitability of muscles and nerves, stimulus transmission of nerves, and blood coagulation, and as an activation factor for enzyme activity. Therefore, the real-time measurement of the distribution and changes of in vivo calcium ions is important in the discovery of diseases, therapeutic courses, research of physiological functions, and the like. The extracellular calcium ion concentration is 1 to 2 mM, while the intracellular calcium ion concentration is 50 to 100 mM, which is one ten-thousandth of the extracellular one.

As a sensor of such calcium ions, there has been reported, for example, a compound having a glycol ether diamine tetraacetic acid (ethylene glycol tetraacetic acid: EGTA) skeleton (Fura-2) (Non Patent Literature 1). However, since this sensor has a high association constant pKa of about 6 to 10, the sensor can detect a calcium ion concentration of the order of nM but cannot detect the extracellular calcium ion concentration. Further, the sensor only has an irreversible sensing capability at the extracellular calcium concentration, and is difficult to be integrated with a device, and therefore the sensor is only used in in vitro intracellular imaging.

CITATION LIST

Non Patent Literature

Non Patent Literature 1: J. Biol. Chem., 1985, 260, 3440

SUMMARY OF THE INVENTION

Problems to be Solved by the Invention

An object of the present invention is to provide: a compound useful as a polyvalent metal ion sensor for calcium ions or the like which is capable of reversible sensing and of being integrated into a device; and an ion sensor using the compound.

Means for Solving the Problems

The present inventors paid attention to a polymer having carboxyl groups on its side chains, which is represented by a polyacrylic acid, produced a copolymer to which a compound having an aggregation-induced emission capability was incorporated as a part thereof, and studied its effects of sensing various metal ions. As a result, the inventors have found that: the copolymer binds to polyvalent metal ions such as calcium ions to thereby generate fluorescence by the aggregation-induced emission compound; the fluorescence is reversible; and further the copolymer can be immobilized on a solid base material or the like and integrated into a device; and the inventors have thus completed the present invention.

That is, the present invention provides the following [1] to [15].

[1] A copolymer comprising a repeating unit (A) having a carboxyl group on a side chain thereof, and a repeating unit (B) having a carboxylate group having an ester residue exhibiting an aggregation-induced emission capability on a side chain thereof.

[2] The copolymer according to [1], wherein the repeating unit (A) is a repeating unit derived from a monomer selected from the group consisting of acrylic acid, methacrylic acid and styrenecarboxylic acid.

[3] The copolymer according to [1] or [2], wherein the repeating unit (B) is a repeating unit derived from a monomer selected from the group consisting of acrylates, methacrylates and styrenecarboxylates having an ester residue derived from a compound represented by the following formula (1) or (2).

In the formula (1), $R^1$s are identical or different, and each represent an optionally substituted aromatic hydrocarbon group or an optionally substituted aromatic heterocyclic group; $E^1$ represents a silicon atom or a germanium atom; $A^1$ and $B^1$ are identical or different, and each represent a hydrocarbon group; and n represents an integer of 1 to 4.

In the formula (2), $R^2$ and $R^3$ are identical or different, and each represent an optionally substituted aromatic hydrocarbon group or an optionally substituted aromatic heterocyclic group; and $A^2$ and $B^2$ are identical or different, and each represent a hydrogen atom, an optionally substituted hydrocarbon group, or an optionally substituted aromatic heterocyclic group.

[4] The copolymer according to [3], wherein the compound represented by the formula (1) or (2) is 1-methyl-1,2,3,4,5-pentaphenylsilole, 2,3,4,5-tetraphenyl-1,1-dimethylsilole or tetraphenylethylene which optionally has 1 to 5 hydrophilic groups substituted on a phenyl group thereof.

[5] The copolymer according to any one of [1] to [4], wherein the copolymer has a molar ratio of the repeating unit (A) to the repeating unit (B), (A/B), of 4 to 1,000.

[6] The copolymer according to any one of [1] to [5], wherein the copolymer has a number-average molecular weight of 10,000 to 1,000,000.

[7] The copolymer according to any one of [1] to [6], wherein the copolymer is a copolymer for detecting polyvalent metal ion fluorescence.

[8] The copolymer according to any one of [1] to [7], further comprising a repeating unit (C) derived from a polyfunctional monomer.

[9] The copolymer according to [8], wherein the copolymer comprises 0.1 to 10 mol % of the repeating unit (C).

[10] The copolymer according to [8] or [9], wherein the repeating unit (C) is a repeating unit derived from a monomer having two or more polymerizable vinyl groups.

[11] A device for detecting polyvalent metal ions, comprising the copolymer according to any one of [1] to [10].

[12] The device for detecting polyvalent metal ions according to [11], wherein the copolymer according to any one of [1] to [10] is immobilized on a solid base material.

[13] The device for detecting polyvalent metal ions according to [12], wherein means for immobilizing the copolymer according to any one of [1] to [10] on the solid base material is covalent bonding of the solid base material with the copolymer.

[14] A method for quantifying a polyvalent metal ion concentration in a sample, comprising bringing a sample into contact with a device according to any one of [11] to [13], and measuring a fluorescence intensity.

[15] A compound represented by the following formula (3).

(3)

In the formula (3), $R^4$ represents a hydrogen atom or a methyl group; $R^5$ represents a direct bond, an alkylene group having 1 to 8 carbon atoms, or a phenylene group; and X represents a group derived from a compound represented by the following formula (1) or (2).

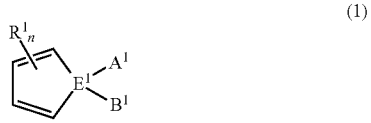

(1)

In the formula (1), $R^1$s are identical or different, and each represent an optionally substituted aromatic hydrocarbon group or an optionally substituted aromatic heterocyclic group; $E^1$ represents a silicon atom or a germanium atom; $A^1$ and $B^1$ are identical or different, and each represent a hydrocarbon group; and n represents an integer of 1 to 4.

(2)

In the formula (2), $R^2$ and $R^3$ are identical or different, and each represent an optionally substituted aromatic hydrocarbon group or an optionally substituted aromatic heterocyclic group; and $A^2$ and $B^2$ are identical or different, and each represent a hydrogen atom, an optionally substituted hydrocarbon group, or an optionally substituted aromatic heterocyclic group.

Effects of the Invention

The use of the copolymer according to the present invention enables polyvalent metal ions represented by calcium ions to be detected at a high sensitivity, and its detectability (light emissivity) is reversible. Further, the copolymer according to the present invention is easily immobilized on a resinous base material and the like. Therefore, the use of the copolymer according to the present invention enables a device for detecting polyvalent metal ions represented by calcium ions to be fabricated.

BRIEF DESCRIPTION OF THE DRAWINGS

FIG. 1 shows fluorescence spectra of poly-$1_{0.05}$ in methanol/water mixed solvents (10 mg/L, excitation light: 307 nm, hereinafter the same is applied).

FIG. 2 shows fluorescence intensities of poly-$1_{0.05}$ with respect to the $Ca^{+2}$ concentrations.

FIG. 3 shows changes in fluorescence intensities of poly-$1_{0.05}$ vs. the $Na^I$, $K^I$, $Mg^I$ or $Ca^{2I}$ concentration.

FIG. 4 shows $Ca^{2+}$ sensing capabilities of poly-$1_{0.05}$ with respect to various polyvalent metal ions.

FIG. 5 shows $Ca^{2+}$ sensing capabilities of poly-$1_{0.05}$ in the presence of $Na^+$ or $Mg^{2+}$.

FIG. 6 shows an effect of EDTA on the $Ca^{2+}$ sensing capability of poly-$1_{0.05}$.

FIG. 7 shows changes in the $Ca^{2+}$ sensing capabilities due to changes of the compositions of poly-1.

FIG. 8 shows changes in the $Ca^{2+}$ sensing capabilities due to changes of the compositions of poly-1.

FIG. 9 shows $Ca^{2+}$ sensing capabilities of poly-$1_{0.20}$ and poly-$1_{0.05}$ in methanol/water=8/2.

FIG. 10 shows changes in fluorescence intensities in (a) 5 mg/L, (b) 10 mg/L and (c) 50 mg/L of poly-$1_{0.05}$.

FIG. 11 shows changes in fluorescence intensities in (a) 5 mg/L, (b) 10 mg/L and (c) 50 mg/L of poly-$1_{0.05}$.

FIG. 12 shows effects of addition of $Et_3N$ and TFA on the calcium sensing capabilities of poly-$1_{0.05}$.

FIG. 13 shows $Ca^{2+}$ sensing capabilities due to changes of the compositions of gel-1.

FIG. 14 shows the reversibility of $Ca^{2+}$ of gel-$1_{0.015}$.

FIG. 15 shows relationships between the fluorescence quantum yields and $Ca^{2I}$ sensing capabilities of gels.

FIG. 16 shows the $Ca^{2+}$ sensing capability of a gel in a solution of Hepes buffer:$H_2O$=50:50.

FIG. 17 shows the reproducibility of the fluorescence quantum yield with respect to the change of the calcium concentration.

FIG. 18 shows a structural conceptual view of a flexible sensor in combination with an OLED and an OPV on a flexible substrate.

FIG. 19 shows normalized absorption and fluorescence spectra of poly-$1_{0.05}$ and poly-1-$NMe_2$ in $H_2O/MeOH$=1/1 (concentration: 10 mg/L).

FIG. 20 shows $CaCl_2$ sensing capabilities (FL spectra) of poly-1-$NMe_2$ at 0, 1, 5 or 10 mM (10 mg/L, 293K, in MeOH/water=1/1, $\lambda_{ex}$=341 nm).

DESCRIPTION OF EMBODIMENTS

The copolymer according to the present invention comprises, at least, a repeating unit (A) having a carboxyl group on a side chain thereof and a repeating unit (B) having a carboxylate group having an ester residue exhibiting an aggregation-induced emission capability on a side chain thereof.

The main chain of the repeating unit (A) is not particularly limited as long as having a carboxyl group (—COOH) on its side chain, but is preferably a main chain by radical polymerization. Such a main chain is preferably one represented by the formula (4).

(4)

In the formula (4), $R^4$ represents a hydrogen atom or a methyl group.

Further, the bonding between the main chain and the carboxyl group may be a direct bond or a bond through a divalent hydrocarbon group such as an alkylene group having 1 to 8 carbon atoms or a phenylene group, but is more preferably a direct bond.

Specifically, the repeating unit (A) is preferably a repeating unit derived from a monomer such as acrylic acid, methacrylic acid and styrenecarboxylic acid, and more preferably a repeating unit represented by the formula (5).

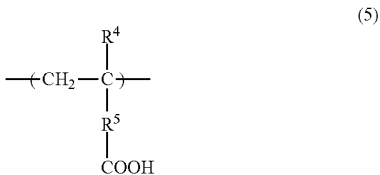

(5)

In the formula (5), $R^4$ represents a hydrogen atom or a methyl group; and $R^5$ represents a direct bond, an alkylene group having 1 to 8 carbon atoms, or a phenylene group.

The repeating unit (B) has a carboxylate group having an ester residue exhibiting an aggregation-induced emission capability on a side chain thereof.

Examples of the ester residue exhibiting the aggregation-induced emission capability include groups derived from compounds represented by the following formula (1) or (2).

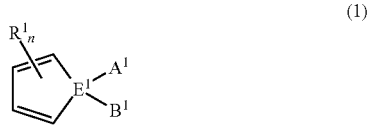

(1)

In the formula (1), $R^1$s are identical or different, and each represent an optionally substituted aromatic hydrocarbon group or an optionally substituted aromatic heterocyclic group; $E^1$ represents a silicon atom or a germanium atom; $A^1$ and $B^1$ are identical or different, and each represent a hydrocarbon group; and n represents an integer of 1 to 4.

(2)

In the formula (2), $R^2$ and $R^3$ are identical or different, and each represent an optionally substituted aromatic hydrocarbon group or an optionally substituted aromatic heterocyclic group; and $A^2$ and $B^2$ are identical or different, and each represent a hydrogen atom, an optionally substituted hydrocarbon group, or an optionally substituted aromatic heterocyclic group.

Examples of the aromatic hydrocarbon group represented by $R^1$, $R^2$ and $R^3$ include aromatic hydrocarbon groups having 6 to 14 carbon atoms, and specifically include a phenyl group, a naphthyl group and a biphenyl group. Further, as the aromatic heterocyclic group, ones having 1 to 3 nitrogen atoms, oxygen atoms or sulfur atoms are preferable, and examples thereof include a pyrrolyl group, an imidazolyl group, a pyridyl group, a pyrimidinyl group, a thienyl group and a thiazolyl group. The groups which may be substituted on these aromatic hydrocarbon groups or aromatic heterocyclic groups are preferably hydrophilic groups, and are more preferably 1 to 5 groups selected from the group consisting of a hydroxy group, an amino group, an alkylamino group, a dialkylamino group, a sulfo group, a thiol group, a polyoxyethylene group, a polyoxypropylene group and a sulfinyl group. Here, the alkylamino group and the dialkylamino group are preferably a $C_1$ to $C_6$ alkylamino group and a di ($C_1$ to $C_6$ alkyl)amino group.

Preferable examples of $R^1$, $R^2$ and $R^3$ are each a phenyl group optionally having the above 1 to 5 hydrophilic substituents.

The hydrocarbon groups represented by $A^1$ and $B^1$ are preferably alkyl groups having 1 to 6 carbon atoms and aromatic hydrocarbon groups. Here, specific examples of the alkyl group include a methyl group, an ethyl group, an n-propyl group, an n-butyl group and an isopropyl group. The aromatic hydrocarbon groups are preferably aromatic hydrocarbon groups as in the case of the above $R^1$, $R^2$ and $R^3$, and particularly preferably phenyl groups optionally having 1 to 5 hydrophilic substituents.

The hydrocarbon groups and the aromatic heterocyclic groups represented by $A^2$ and $B^2$ are preferably the aromatic hydrocarbon groups or the aromatic heterocyclic groups mentioned as the above $R^1$, $R^2$ and $R^3$. Further, the groups which may be substituted on these hydrocarbon groups or heterocyclic groups are preferably hydrophilic groups, and more preferably 1 to 5 groups selected from the group consisting of a hydroxy group, an amino group, an alkylamino group, a dialkylamino group, a sulfo group, a thiol group, a polyoxyethylene group, a polyoxypropylene group and a sulfinyl group. Here, the alkylamino group and the dialkylamino group are preferably a $C_1$ to $C_6$ alkylamino group and a di($C_1$ to $C_6$ alkyl)amino group.

Preferable examples of $A^2$ and $B^2$ are each a phenyl group optionally having the above 1 to 5 hydrophilic groups.

n is particularly preferably 4.

Particularly preferable examples of the compound represented by the formula (1) are 2,3,4,5-tetraphenyl-1,1-dimethylsilole or 1-methyl-1,2,3,4,5-pentaphenylsilole (TPS) optionally having the above 1 to 5 hydrophilic groups substituted on the phenyl groups thereof. Particularly preferable examples of the compound represented by the formula (2) are tetraphenylethylene (TPE) optionally having the above 1 to 5 hydrophilic groups substituted on the phenyl groups thereof.

The main chain of the repeating unit (B) is not particularly limited as long as having the above carboxylate group on its side chain, but is preferably a main chain by radical polymerization. Such a main chain is preferably one represented by the formula (6).

(6)

In the formula (6), $R^4$ represents a hydrogen atom or a methyl group.

Further, the bonding between the main chain and the carboxylate group may be a direct bond or a bond through a divalent hydrocarbon group such as an alkylene group having 1 to 8 carbon atoms or a phenylene group, but is more preferably a direct bond.

Specifically, the repeating unit (B) is preferably a repeating unit derived from a monomer such as an acrylate, a methacrylate and a styrenecarboxylate, and more preferably a repeating unit represented by the formula (7)

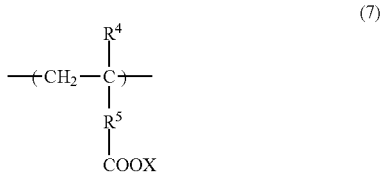

(7)

In the formula (7), $R^4$ represents a hydrogen atom or a methyl group; $R^5$ represents a direct bond, an alkylene group having 1 to 8 carbon atoms, or a phenylene group; and X represents a group derived from a compound represented by the above formula (1) or (2).

The molar ratio of the repeating unit (A) to the repeating unit (B), (A/B), in the copolymer according to the present invention is, from the viewpoints of the sensitivity to calcium ions and the like, preferably 2 or higher and 1,000 or lower, more preferably 3 to 1,000, even more preferably 4 to 1,000, and even more preferably 5 to 1,000.

Further, the copolymer according to the present invention may have another repeating unit as long as comprising the repeating unit (A) and the repeating unit (B). Examples of the another repeating unit include a repeating unit (C) derived from a polyfunctional monomer and a repeating unit derived from ethylene, styrene, an alkyl (meth)acrylate, (meth)acrylamide and the like. Among these, the copolymer comprising, in addition to the repeating unit (A) and the repeating unit (B), a repeating unit (C) derived from a polyfunctional monomer forms a crosslinked structure and thereby gelates, and thus is particularly preferable as a polyvalent metal ion sensor.

The repeating unit (C) may be a repeating unit derived from a monomer having two or more polymerizable vinyl groups, and examples thereof include polyol poly-unsaturated carboxylates, linear or branched alkylenepolyacrylamides, polyol polyacrylamides, and divinylbenzenes. Among these, the polyol poly-unsaturated carboxylates are preferably polyol poly(meth)acrylates. Here, the polyols are preferably di- to pentavalent polyols such as ethylene glycol, polyethylene glycol, propylene glycol, polypropylene glycol, butylene glycol (including 1,3-butanediol and 1,4-butanediol), polybutylene glycol, neopentyl glycol, glycerol, polyglycerol, pentaerythritol, 1,6-hexanediol, trimethylolpropane, bisphenol A, tricyclo[5.2.1.0$^{2,6}$]decanedimethanol, tris(2-hydroxyethyl)isocyanurate, bis(2-hydroxyethyl) phosphate, hexafluorohexanediol, decanediol and pentanediol.

The linear or branched alkylenepolyacrylamides are preferably linear or branched alkylenepolyacrylamides having 1 to 4 carbon atoms, and examples thereof include methylenebisacrylamide, ethylenebisacrylamide and propylenebisacrylamide. Further, examples of the polyol diacrylamide include (1,2-dihydroxyethylene)bisacrylamide. Examples of the divinylbenzene include ortho-, meta- and para-divinylbenzene.

The repeating unit (C) is contained in the copolymer according to the present invention, from the viewpoints of the gel formability and the ion measurement sensitivity, preferably in an amount of 0.1 to 10 mol %, more preferably 0.1 to 8 mol %, even more preferably 0.5 to 5 mol %, and even more preferably 1 to 5 mol %.

Further, the degree of swelling of a gel increases depending on the content of the repeating unit (C), and the degree of swelling is, from the viewpoint of the $Ca^{2+}$ sensing capability, preferably 340% or higher, more preferably 340 to 1,500%, and even more preferably 500 to 1,500%.

Further, the copolymer according to the present invention may have functional groups to become bonding sites with a base material; and examples of such a functional group include alcohols, thiols, amines, carboxylic acids, sulfonic acids, phosphonic acids, siloxanes, vinyls and acetylene.

The number-average molecular weight (Mn) of the copolymer according to the present invention is, from the viewpoints of the sensitivity to calcium ions and the like, preferably 10,000 or higher and 1,000,000 or lower, more preferably 10,000 to 800,000, and even more preferably 10,000 to 500,000. The number-average molecular weight can be measured by a method described in Examples described later.

The form of copolymerization of the copolymer according to the present invention may be any of random copolymerization, alternating copolymerization, block copolymerization and graft copolymerization, but is preferably random copolymerization.

Then, production methods of the copolymer according to the present invention will be described.

The copolymer according to the present invention can be produced, for example, by radically copolymerizing a monomer as a repeating unit (A), a monomer as a repeating unit (B), and further as required, a monomer as a repeating unit (C). Alternatively, the copolymer can be produced by radically copolymerizing a monomer as a repeating unit (A) whose carboxyl group is protected, a monomer as a repeating unit (B), and as required, a monomer as a repeating unit (C), and thereafter, removing the protecting group of the carboxyl group of the repeating unit (A).

Here, the monomer as the repeating unit represented by the above formula (7) is represented by the following formula (3).

(3)

In the formula (3), $R^4$, $R^5$ and X are the same as in the above.

The monomer (3) can be obtained, for example, by reacting a (meth)acryl halide with XOH in the presence of a base such as triethylamine.

The protecting group of the carboxyl group of the repeating unit (A) is preferably a tert-butyl group.

The above radical copolymerization reaction is carried out in the presence of a polymerization initiator. Examples of the polymerization initiator include azo initiators such as 2,2'-azobis(isobutyronitrile), dimethyl 2,2'-azobis(2-methylpropionate) and 2,2'-azobis(4-methoxy-2,4-dimethylvaleronitrile); photopolymerization initiators such as 2,2-dimethoxy-1,2-diphenylethan-1-one; and peroxides such as di(3,5,5-trimethylhexanoyl) peroxide and benzoyl peroxide, and these polymerization initiators can be used singly or in a combination of two or more.

The total amount of the polymerization initiator used is usually about 0.0002 to 0.2 times the mass of the monomer of the repeating unit (A).

Further, a solvent and a chain transfer agent may be used in the radical copolymerization reaction. Examples of the solvent include amide solvents such as dimethylformamide, dimethylacetamide and N-methylpyrrolidone; sulfoxide solvents such as dimethyl sulfoxide; ester solvents such as ethyl acetate, butyl acetate and γ-butyrolactone; aromatic solvents such as toluene and benzene; and ether solvents such as 1,4-dioxane and diethyl ether, and these solvents can be used singly or in a combination of two or more. The total amount of the solvents used is usually about 0.5 to 15 times the mass of the monomer of the repeating unit (A).

Further, examples of the chain transfer agent include mercaptoethanol, thioglycerol and tert-dodecyl mercaptan.

Further, the copolymerization reaction time is usually about 0.5 to 24 hours; and the reaction temperature can suitably be selected at a temperature of the boiling point of a solvent or lower, but is usually about 0 to 120° C.

After the copolymerization reaction, the removal of the protecting group of the carboxyl group, for example, a tert-butyl group, of the repeating unit (A) can easily be carried out by a trifluoroacetic acid treatment.

The copolymer according to the present invention generates no fluorescence in the absence of calcium ions and the like, and generates strong fluorescence depending on the concentration of calcium ions and the like. That is, the carboxyl groups in the copolymer bind to polyvalent metal ions to form a crosslinked structure, resulting in the generation of fluorescence by the aggregation of the groups having the aggregation-induced emission capability. Further, the copolymer according to the present invention having the repeating unit (C) can be immobilized on specific sites due to its gel form, and therefore can measure polyvalent metal ions stably over a long period of time.

Thus, the copolymer according to the present invention is useful as a sensor of ions of various polyvalent metals, since the copolymer reacts with ions of polyvalent metals such as calcium and generates fluorescence as shown in Examples described later. Further, the copolymer according to the present invention is useful as a device for detecting polyvalent metal ions, since the fluorescence disappears in the presence of a chelating agent and the generation of fluorescence is reversible. Further, the copolymer having the repeating unit (C) has a form of gel and is useful as a polyvalent metal ion sensor which is stable over a long period of time.

In order to make the copolymer according to the present invention into a polyvalent metal ion sensor device (device for detecting polyvalent metal ions), the copolymer according to the present invention is formed on a base material. In order to form the copolymer according to the present invention on the base material, it is preferable that a monomer as the repeating unit (A) and a monomer as the repeating unit (B) be copolymerized on the base material. The copolymer can be produced, for example, by introducing an α-bromo-α,α-dimethylacetate group on the base material, and then subjecting the monomer as the repeating unit (A) and the monomer as the repeating unit (B) to a surface-initiated copolymerization thereon.

Further, the copolymer according to the present invention having the repeating unit (C) can be utilized as a polyvalent metal ion sensor as it is since the copolymer has a form of gel, and can also be integrated into an ion sensor device by immobilizing the copolymer by gel polymerization on the base material. The gel formed from the copolymer according to the present invention can be applied to a device for extracellularly detecting the calcium concentration, since the gel can sense calcium in a concentration range near the extracellular calcium concentration of the order of mM. That is, it is conceivable that a flexible calcium sensor can be constructed by combining the gel with an organic light emitting diode (OLED) and an organic photovoltaic (OPV) on a flexible substrate. Also, the construction of a large-area calcium sensing device is enabled by integrating the sensors.

Here, examples of the base material include glasses, transparent resin films, and transparent resin needles. Examples of the material of the transparent resin include polyethylene, polypropylene, polystyrene, polyester such as polyethylene terephthalate, polyvinyl chloride, polyvinylidene chloride, polyvinyl alcohol, polycarbonate, polyacrylonitrile, and ethylene-vinyl acetate copolymers.

By bringing a sample into contact with a device for detecting polyvalent metal ions, and measuring the generated fluorescence intensity, the polyvalent metal ion concentration in the sample can be quantified. Here, examples of the sample, in the case of calcium ions, include blood, plasma, serum, lymph, body fluids such as urine, and various types of tissues. Further, examples of polyvalent metal ions other than calcium ions include ions of heavy metals such as zinc, lead, cadmium, mercury, copper, chromium, manganese, arsenic and cobalt. Examples of the sample, in the cases of these heavy metal ions, include various types of environmental water such as river water, lake water and wastewater, and soil.

The measurement is carried out, specifically, by bringing the sample into contact with the device, thereafter irradiating the device with excitation light, and measuring the generated fluorescence. Therefore, a fluorescence measuring kit includes the device, an excitation light irradiator and a fluorescence measuring instrument. Use of a calibration curve prepared in advance is a simple technique for quantifying the polyvalent metal ion concentration from an obtained fluorescence intensity.

EXAMPLES

Then, the present invention will be described in detail by way of Examples.

Example 1

(1) A zinc powder (15.6 g) and 200 ml of tetrahydrofuran were placed in a reaction vessel under an argon gas atmosphere. The mixture was cooled to −5 to 0° C., and $TiCl_4$ (13.2 ml) was slowly added by using a syringe maintained at 10° C. or lower. The mixture was stirred at room temperature for 0.5 hours, and refluxed under heating for 2.5 hours. The mixture was again cooled to −5 to 0° C. Pyridine (5.0 ml) was added and the resultant was stirred for 10 min. A tetrahydrofuran (30 ml) solution of p-hydroxybenzophenone (4.80 g) and benzophenone (5.28 g) was slowly added by using a syringe. After the addition, the reaction mixture was heated to 70° C., and refluxed until the raw materials disappeared on TLC. A 10% $K_2CO_3$ aqueous solution was added, and then, dichloromethane was added. An organic layer was washed with water and a saline solution, dried over $MgSO_4$, thereafter dried up under reduced pressure, and purified by silica gel column chromatography ($CHCl_3$) to thereby obtain 2.76 g (yield: 32%) of p-hydroxytetraphenylethylene (p-hydroxyTPE).

$^1$H NMR (400 MHz, $CDCl_3$) δ 6.98-7.15 (m, 15H), 6.89 (dd, J=8.68, 2.07 Hz, 2H), 6.56 (dd, J=8.76, 2.23 Hz, 2H), 4.63 (s, 1H) ppm.

(2) A dichloromethane (30 ml) solution of the p-hydroxytetraphenylethylene (0.910 g) and triethylamine (1.46 ml) was cooled to 0° C., and a dichloromethane (5 ml) solution of acryloyl chloride (420 μL) was added dropwise. The reaction mixture was stirred at room temperature for 3 hours until the raw materials disappeared on TLC. Sodium hydrogen carbonate was added to the reaction liquid, and dichloromethane was further added. An organic layer was washed with water and a saline solution, dried over $MgSO_4$, thereafter dried up under reduced pressure, and purified by silica gel column chromatography (hexane:$CHCl_3$=1:1) to thereby obtain 0.756 g (yield: 72%) of p-hydroxytetraphenylethylene acrylate (p-hydroxyTPE acrylate). Tetraphenylethylene is abbreviated to TPE.

$^1$H NMR (400 MHz, $CDCl_3$, 293 K) δ 7.01-7.11 (m, 15H), 6.89 (d, J=9.0 Hz, 2H), 6.56 (dd, J=17.3, 1.3 Hz, 1H), 6.27 (dd, J=10.5, 17.3 Hz, 1H), 5.99 (dd, J=10.5, 1.3 Hz, 1H) ppm.

$^{13}$C NMR (100 MHz, $CDCl_3$, 293K) δ 164.3, 149.0, 143.7, 143.6, 143.5, 141.4, 141.3, 140.0, 132.4, 132.3, 131.4, 131.3, 128.1, 127.9, 127.8, 127.7, 126.6, 126.5, 120.7 ppm.

FT-IR (KBr) ν 3076, 3054, 3024, 1756, 1677, 1599, 1502, 1443, 1356, 1200, 1166, 1140, 1017, 763, 748, 699, 613, 572, 498 $cm^{-1}$.

HRMS(FAB) Cald for $C_{29}H_{22}O_2$ [M]=402.1620, Found: m/z=402.167.

Example 2

(1) A dimethylformamide (1 ml) solution of the p-hydroxyTPE (21.3 mg, 5 mol %), tert-butyl acrylate (146 μL, 95 mol %) and 2,2'-azobis(isobutyronitrile) (AIBN) was deoxygenated three times by using a reduced pressure/argon gas. The solution was stirred at 60° C. for 12 hours, and cooled to room temperature; and the solvent was distilled off to thereby obtain 156 mg of a (p-hydroxyTPE acrylate)$_{0.05}$-(tert-butyl acrylate)$_{9.95}$-copolymer.

$^1$H NMR (400 MHz, $CDCl_3$, 293 K) δ 6.79-7.11, 2.05-2.39, 1.71-1.86, 1.20-1.63 ppm.

FT-IR (KBr) ν 2979, 2935, 1731, 1481, 1457, 1393, 1368, 1257, 1149, 1034, 909, 846, 751, 701, 471, 430 $cm^{-1}$.

$M_n$=24,000, $M_w$=44,000, PDI=1.86 (GPC: eluent; DMF, PSt standards).

(2) 10.0 mg of the copolymer obtained in (1) was dissolved in trifluoroacetic acid (58.0 μL), and stirred at room temperature for 12 hours. The solvent was distilled off from the reaction liquid to thereby obtain 9.80 mg of a (p-hydroxyTPE acrylate)$_{0.05}$-(acrylic acid)$_{9.95}$-copolymer.

$^1$H NMR (400 MHz, $CD_3OD$, 293 K) δ 6.79-7.21, 2.28-2.65, 1.40-2.22 ppm.

FT-IR (KBr) ν 2961, 2361, 1716, 1503, 1454, 1417, 1249, 1168, 802, 701, 614, 503, 414 $cm^{-1}$.

Example 3

(1) A (p-hydroxyTPE acrylate)$_{0.01}$-(tert-butyl acrylate)$_{9.99}$-copolymer was obtained in a similar manner to Example 2(1).

$^1$H NMR (400 MHz, $CDCl_3$, 293 K) δ 6.78-7.15, 2.08-2.35, 1.71-1.89, 1.20-1.62 ppm.

FT-IR (KBr) ν 2980, 2936, 1731, 1481, 1458, 1394, 1368, 1258, 1148, 1035, 909, 847, 752, 701, 471, 435 $cm^{-1}$.

$M_n$=21000, $M_w$=29000, PDI=1.36 (GPC: eluent; DMF, PSt standards).

(2) A (p-hydroxyTPE acrylate)$_{0.01}$-(acrylic acid)$_{9.99}$-copolymer was obtained in a similar manner to Example 2(2).

$^1$H NMR (400 MHz, $CD_3OD$, 293 K) δ 6.82-7.21, 2.22-2.64, 1.42-2.10 ppm

FT-IR (KBr) ν 2961, 2349, 1717, 1456, 1417, 1253, 1169, 802, 701, 617, 511, 463, 436, 404 $cm^{-1}$.

Example 4

(1) A (p-hydroxyTPE acrylate)$_{0.2}$-(tert-butyl acrylate)$_{0.80}$-copolymer was obtained in a similar manner to Example 2(1).

$^1$H NMR (400 MHz, $CDCl_3$, 293 K) δ 6.45-7.24, 0.60-2.76 ppm.

FT-IR (KBr) ν 3439, 3055, 2978, 2933, 2360, 1757, 1728, 1599, 1503, 1493, 1408, 1444, 1393, 1368, 1256, 1200, 1149, 1075, 1031, 1018, 846, 762, 749, 700, 614, 572, 473, 430 $cm^{-1}$.

$M_n$=34,000, $M_w$=67,000, PDI=1.98 (GPC: eluent; DMF, PSt standards).

(2) A (p-hydroxyTPE acrylate)$_{0.20}$-(acrylic acid)$_{0.80}$-copolymer was obtained in a similar manner to Example 2(2).

$^1$H NMR (400 MHz, $CD_3OD$, 293 K) δ 6.62-7.21, 1.10-2.79 ppm.

FT-IR (KBr) ν 3054, 2932, 2362, 1718, 1599, 1502, 1444, 1406, 1198, 1166, 1075, 1030, 1017, 803, 763, 748, 699, 613, 572 $cm^{-1}$.

Example 5

(1) A (p-hydroxyTPE acrylate)$_{0.50}$-(tert-butyl acrylate)$_{0.50}$-copolymer was obtained in a similar manner to Example 2(1).

$^1$H NMR (400 MHz, $CDCl_3$, 293 K) δ 6.50-7.20, 1.05-2.95 ppm.

FT-IR (KBr) ν 3440, 3054, 3022, 2977, 2932, 2360, 1757, 1727, 1599, 1502, 1493, 1444, 1393, 1368, 1251, 1200, 1165, 1147, 1075, 1030, 1018, 845, 762, 748, 699, 614, 572, 496 $cm^{-1}$.

$M_n$=18,000, $M_w$=35,000, PDI=1.95 (GPC: eluent; DMF, PSt standards).

(2) A (p-hydroxyTPE acrylate)$_{0.50}$-(acrylic acid)$_{0.50}$-copolymer was obtained in a similar manner to Example 2(2).

$^1$H NMR (400 MHz, $CDCl_3$, 293 K) δ 6.39-7.24, 0.65-3.05 ppm.

FT-IR (KBr) ν 3438, 3053, 3024, 2931, 2361, 1950, 1752, 1599, 1576, 1502, 1493, 1444, 1199, 1166, 1075, 1030, 1017, 762, 749, 698, 613, 572, 496 $cm^{-1}$.

The structures and the physical properties of the copolymers obtained in Example 2 to Example 5 are shown in Table 1.

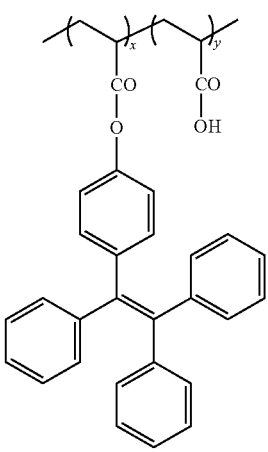

TABLE 1

| Copolymer | | Ratio at Addition (A) | (B) | Copolymer Composition $A_{(x)}$ | $B_{(y)}$ | $M_n$ | PDI |
|---|---|---|---|---|---|---|---|
| Example 2 | Poly-$1_{0.01}$ | 0.01 | 0.99 | 0.01 (3) | 0.99 (276) | 21,000 | 1.36 |
| Example 3 | Poly-$1_{0.05}$ | 0.05 | 0.95 | 0.05 (14) | 0.95 (258) | 24,000 | 1.86 |
| Example 4 | Poly-$1_{0.20}$ | 0.20 | 0.80 | 0.20 (49) | 0.80 (196) | 34,000 | 1.98 |
| Example 5 | Poly-$1_{0.50}$ | 0.50 | 0.50 | 0.50 (38) | 0.50 (38) | 18,000 | 1.95 |

Example 6 (Light Emission of Poly-$1_{0.05}$ in a Methanol/Water Mixed Solvent)

The solubility of poly-$1_{0.05}$ was examined and it was found that poly-$1_{0.05}$ exhibited solubility in methanol, but was insoluble to water. Since the present invention has an object of the in vivo recognition of $Ca^{2+}$, experiments needed to be carried out in an aqueous system, but to begin with, experiments were carried out using mixed solvent systems of methanol and water.

UV spectra and fluorescence spectra of poly-$1_{0.05}$ were measured in methanol/water mixed solvents in various compositional ratios (methanol/water=100/0 to methanol/water=1/99).

In the UV-vis spectra, as water was added, light scattering accompanying precipitation formation was observed, but no large changes other than that were observed.

In contrast, in the fluorescence spectra, large changes were observed (FIG. 1). That is, poly-$1_{0.05}$ exhibited almost no fluorescence in a 100% solution of methanol, but the fluorescence largely increased as water was added.

In the experiments hereafter, the reactivity with $Ca^{2+}$ was evaluated in a mixed solvent of methanol/water=5/5.

Example 7 ($Ca^{2+}$ Sensing Capability)

(1) As described above, poly-$1_{0.05}$ is insoluble in water. Thus, poly-$1_{0.05}$ was dissolved in a mixed solvent of methanol/water=5/5, and the change in fluorescence behavior when $Ca^{2+}$ was added was studied. Specifically, fluorescence spectra were observed when $CaCl_2$ was added little by little to a 10 mg/L poly-$1_{0.05}$ solution. The changes of the fluorescence spectra are shown in FIG. 2.

In the fluorescence spectra in FIG. 2, the increases in the fluorescence intensity were observed as $CaCl_2$ was added. With respect to the increases in the fluorescence intensity, it is conceivable that, in poly-$1_{0.05}$ in the presence of $Ca^{2+}$, the aggregation of polymer chains is induced and the intramolecular rotational motion of TPE sites is suppressed, resulting in increasing the fluorescence intensity. In order to examine whether the changes in the spectra were caused by a decrease in the solubility simply due to salting out, other metal ions (NaCl, KCl or $MgCl_2$) were added little by little to poly-$1_{0.05}$ and the changes in the fluorescence intensities were observed. FIG. 3 shows a graph in which fluorescence intensities at a maximum fluorescence wavelength ($\lambda_{max}$=465 nm) are plotted vs. the metal salt concentration.

From FIG. 3, it was found that when $Na^+$, $K^+$ or $Mg^{2+}$ was added to poly-$1_{0.05}$, the increase in the fluorescence intensity was surprisingly slight as compared with $Ca^{2+}$, and poly-$1_{0.05}$ could selectively sense $Ca^{2+}$. That is, it was suggested that the changes in the fluorescence spectra were not caused by a decrease in the solubility simply due to salting out, but caused by that the addition of $Ca^{2+}$ induced the aggregation of polymer chains and suppressed the intramolecular rotational motion of TPE sites.

(2) Also from FIG. 3, it is found that there is a large difference in the changes in the fluorescence spectra between $Ca^{2+}$ and $Mg^{2+}$, which are divalent metal ions of the same valency. In order to examine this selectivity, a chloride of $Sr^{2+}$ or $Ba^{2+}$, which are other alkaline earth metals, or a chloride of $Zn^{2+}$ or $Fe^{2+}$, which are transition metals, was added to poly-$1_{0.05}$ and the fluorescence spectrum was measured. In FIG. 4, there are plotted fluorescence intensities at a maximum fluorescence wavelength ($\lambda_{max}$=465 nm) vs. the metal salt concentration.

When $Ca^{2+}$ was added to poly-$1_{0.05}$, the fluorescence intensity was almost saturated by the addition of about 1.0 mM of $CaCl_2$, but in the case of $Sr^{2+}$ or $Ba^{2+}$, the fluorescence intensity was saturated by the addition of about 0.1 mM thereof. Further, in the case of $Zn^{2+}$, the fluorescence intensity was saturated by the addition of about 0.4 mM thereof. That is, it was found that poly-$1_{0.05}$ responded more sensitively to $Sr^{2+}$, $Ba^{2+}$ and $Zn^{2+}$ than to $Ca^{2+}$.

In the alkaline earth metals, the ionic radius thereof becomes large in the order of $Mg^{2+}$, $Ca^{2+}$, $Sr^{2+}$ and $Ba^{2+}$, while the responsivility of poly-$1_{0.05}$ was nearly in this order, suggesting that an alkaline earth metal ion having a larger ionic radius interacted more strongly with poly-$1_{0.05}$ and promoted the aggregation of the polymer. The change in the fluorescence spectrum by the addition of $Zn^{2+}$, which is a transition metal, was larger than in the case of $Ca^{2+}$. In contrast, the addition of $Fe^{2+}$ reduced the fluorescence intensity of poly-$1_{0.05}$, and thus it is conceivable that $Fe^{2+}$ functions as a quencher. It was thus found that among the transition metal ions, there were metal ions which increased the fluorescence intensity by the addition thereof to poly-$1_{0.05}$, such as $Zn^{2+}$, and metal ions which reduced the fluorescence intensity, such as $Fe^{2+}$.

(3) Then, it was studied whether poly-$1_{0.05}$ could selectively sense $Ca^{2+}$ even in the presence of $Na^+$ or $Mg^{2+}$. There was observed the change in the fluorescence spectrum when 1.0 mM of $Ca^{2+}$ was added to a solution of poly-$1_{0.05}$ in which 1.0 mM of $Na^+$ or $Mg^{2+}$ had been added (FIG. 5).

First, when 1.0 mM of NaCl or $MgCl_2$ was added to poly-$1_{0.05}$, the fluorescence intensity hardly increased.

When 1.0 mM of CaCl$_2$ was added thereto, the fluorescence intensity largely increased. This fact indicates that poly-$1_{0.05}$ can selectively sense Ca$^{2+}$ even in the presence of Na$^+$ or Mg$^{2+}$. This suggests the possibility of poly-$1_{0.05}$ being able to selectively sense Ca$^{2+}$ also in vivo where much foreign matters are present.

(4) Further, in order to examine the reversibility of Ca$^{2+}$ sensing of poly-$1_{0.05}$, EDTA was added to poly-$1_{0.05}$ having Ca$^{2+}$ added therein. EDTA is a Ca$^{2+}$ chelating agent, and the association constant of Ca$^{2+}$ is pK$_a$=10.76. 1.0 mM of EDTA was added to poly-$1_{0.05}$ having 1.0 mM of Ca$^{2+}$ added therein, and the change in the fluorescence spectrum was observed (FIG. 6).

When 1.0 mM of EDTA was added to poly-$1_{0.05}$ having 1.0 mM of Ca$^{2+}$ added therein, the fluorescence intensity reduced to the intensity before the addition of Ca$^{2+}$ (FIG. 6). It is conceivable that the reduction was caused by that Ca$^{2+}$ interacting with poly-$1_{0.05}$ was chelated by EDTA and the poly-$1_{0.05}$ returned to the state before the addition of Ca$^{2+}$. This suggests that the Ca$^{2+}$ sensing of poly-$1_{0.05}$ has the reversibility.

Example 8 (Change in the Ca$^{2+}$ Sensing Capability by the Compositional Change of Poly-1)

In order to examine how differences in compositional ratios of TPE sites to polyacrylic acid sites influenced on the Ca$^{2+}$ sensing capability of poly-1, there was studied the response behavior of poly-$1_{0.01}$, poly-$1_{0.05}$, poly-$1_{0.20}$ and poly-$1_{0.50}$ to Ca$^{2+}$. First, changes in the fluorescence spectra of poly-$1_{0.01}$, poly-$1_{0.05}$, poly-$1_{0.20}$ and poly-$1_{0.50}$ were observed by using mixed solvents of methanol and water or mixed solvents of DMF and water in various compositional ratios. Since poly-$1_{0.50}$ did not dissolve in methanol, a DMF/water mixed solvent was used. Then, FIG. 7(a) to (d) show graphs each in which the fluorescence intensities at a maximum fluorescence wavelength ($\lambda_{max}$=465 nm) are plotted vs. the compositional ratio of water in the methanol/water or DMF/water mixed solvent.

As seen in FIG. 7(a) to (d), in poly-$1_{0.01}$ and poly-$1_{0.05}$, the fluorescence intensities increase from when a water content is about 40%, whereas in poly-$1_{0.20}$ and poly-$1_{0.50}$, the fluorescence intensities start to increase from when a water content is about 10%, and are already saturated when a water content is 50%. This is conceivably because poly-$1_{0.20}$ and poly-$1_{0.50}$ are more hydrophobic.

Then, CaCl$_2$ was added to poly-$1_{0.01}$, poly-$1_{0.05}$, poly-$1_{0.20}$ and poly-$1_{0.50}$ by using a mixed solvent of methanol/water=1/1 or DMF/water=1/1, and the changes in the fluorescence spectra were observed. FIG. 8 shows a graph in which fluorescence intensities normalized with saturation values at a maximum fluorescence wavelength ($\lambda_{max}$=465 nm) are plotted vs. the Ca$^{2+}$ concentration.

In poly-$1_{0.01}$ and poly-$1_{0.05}$, when CaCl$_2$ was added, the fluorescence intensities increased, whereas in poly-$1_{0.20}$ and poly-$1_{0.50}$, even when CaCl$_2$ was added, almost no change in the fluorescence intensities was observed. This is conceivably because the fluorescence intensities in poly-$1_{0.20}$ and poly-$1_{0.50}$ having a water content of 50% were already in a saturated state due to the solvent effect, and the poly-$1_{0.20}$ and poly-$1_{0.50}$ were already aggregated and therefore could not be further aggregated even when Ca$^{2+}$ was added.

Then, in low-water content conditions, a Ca$^{2+}$ titration experiment of poly-$1_{0.20}$ or poly-$1_{0.50}$ was carried out. It is found that the fluorescence intensities are not saturated in a mixed solvent of methanol/water=8/2 or DMF/water=8/2 (FIG. 7 (c), (d)). Then, CaCl$_2$ was added to poly-$1_{0.20}$ or poly-$1_{0.50}$ in the mixed solvent of this compositional ratio, and changes in the fluorescence spectra were observed. FIG. 9 shows a graph in which the fluorescence intensities at a maximum fluorescence wavelength ($\lambda_{max}$=465 nm) are plotted vs. the Ca$^{2+}$ concentration.

When Ca$^{2+}$ was added to poly-$1_{0.20}$ whose solvent compositional ratio was methanol/water=8/2 and poly-$1_{0.50}$ whose solvent compositional ratio was DMF/water=8/2, the fluorescence intensities increased and were saturated at a Ca$^{2+}$ concentration of 0.1 mM. Therefore, it was found that even poly-1 having many TPE sites could sense Ca$^{2+}$ in a low-water content condition.

Further, it is found that the detection ranges of the Ca$^{2+}$ concentration of poly-$1_{0.01}$ and poly-$1_{0.05}$ are 0 mM to 1.0 mM (FIG. 8), whereas those of poly-$1_{0.20}$ and poly-$1_{0.50}$ are 0 mM to 0.1 mM (FIG. 9). This conceivably results from that poly-$1_{0.20}$ and poly-$1_{0.50}$ are more hydrophobic and have fewer carboxylic acid sites which interact with Ca$^{2+}$ and cause the aggregation of the polymer chains than poly-$1_{0.01}$ and poly-$1_{0.05}$. That is, it was found that changing the compositions of poly-1 caused changes in the detection range of the Ca$^{2+}$ concentration.

Example 9 (Change in the Ca$^{2+}$ Sensing Capability by the Concentration Change of Poly-$1_{0.05}$)

There was studied how the Ca$^{2+}$ sensing capability of poly-1 changed depending on the difference in the concentration of poly-$1_{0.05}$. Then, CaCl$_2$ was added to three solutions of poly-$1_{0.05}$ having different concentrations of (a) 5 mg/L, (b) 10 mg/L and (c) 50 mg/L, and changes in the fluorescence spectra were observed. FIG. 10 shows graphs in which the fluorescence intensities normalized with the fluorescence intensities in the saturated states at a maximum fluorescence wavelength ($\lambda_{max}$=465 nm) are plotted vs. the Ca$^{2+}$ concentration.

In poly-$1_{0.05}$ having a concentration of 5 mg/L, the fluorescence intensity was saturated by the addition of about 0.3 mM of Ca$^{2+}$, and in poly-$1_{0.05}$ having a concentration of 50 mg/L, the fluorescence intensity was saturated by the addition of about 30 to 50 mM of Ca$^{2+}$. This is conceivably because poly-$1_{0.05}$ having a low concentration has a smaller number of the polymer and fewer carboxylic acid sites which interact with Ca$^{2+}$ and cause the aggregation of the polymer chains than poly-$1_{0.05}$ having a high concentration, and thus the fluorescence intensity of the poly-$1_{0.05}$ having a low concentration is saturated by the addition of a smaller amount of Ca$^{2+}$.

Then, graphs in which the axis of abscissa of FIG. 10 is converted to the ratio of the Ca$^{2+}$ amount to the carboxylic acid (COOH) of PAA sites are shown in FIG. 11.

It was found that even if the normalization with the ratio of the Ca$^{2+}$ concentration to the polymer was performed, when the concentration of poly-$1_{0.05}$ was different, the ratio of the Ca$^{2+}$ amount to the carboxylic acid (COOH), at which ratio the fluorescence intensity was saturated, was different. That is, in poly-$1_{0.05}$ having a concentration of 5 mg/L, the fluorescence intensity is saturated when the ratio of the Ca$^{2+}$ amount to the carboxylic acid (COOH) is about 10, whereas in poly-$1_{0.05}$ having a concentration of 50 mg/L, the fluorescence intensity is saturated when the ratio of the amount of Ca$^{2+}$ to the carboxylic acid (COOH) is 50 to 100. This is attributed to that in the case where a carboxylic acid interacts with Ca$^{2+}$, the carboxylic acid interacts in the state of a carboxylate (COO$^-$) in which a proton has dissociated, and when the concentration of poly-$1_{0.05}$ becomes low, the degree of dissociation of the carboxylic acid (COOH) increases and the interaction of the carboxylic acid (COOH) with $Ca^{2+}$ is easily caused.

Based on this consideration, it is conceivable that by adding a base or an acid to poly-$1_{0.05}$ and varying the degree of dissociation of the carboxylic acid (COOH), the $Ca^{2+}$ sensing behavior also changes. Then, TFA or triethylamine was added to poly-$1_{0.05}$ having 0.1 mM or 1.0 mM of $Ca^{2+}$ added therein, and the changes in the fluorescence spectra were observed. FIG. 12 shows the fluorescence spectra.

When triethylamine was added to poly-$1_{0.05}$ having 0.1 mM of $CaCl_2$ added therein, the fluorescence intensity increased, and at the time point when 0.5 mM of triethylamine was added, the fluorescence intensity was saturated. When TFA was added to poly-$1_{0.05}$ having 1 mM of $CaCl_2$ added therein, the fluorescence intensity reduced. These changes conceivably result from that the addition of triethylamine to poly-$1_{0.05}$ increases the degree of dissociation of the carboxylic acid (COOH) to thereby produce many carboxylates, make the interaction with $Ca^{2+}$ strong and induce the aggregation of the polymer chains, and the addition of TFA to poly-$1_{0.05}$ reduces the degree of dissociation of the carboxylic acid (COOH) to thereby make the interaction with $Ca^{2+}$ weak and release $Ca^{2+}$. It was thus found that the changes of the acidity and basicity changed the $Ca^{2+}$ sensing capability of poly-$1_{0.05}$.

Example 10 (Effect of Introduction of a Hydrophilic Group to TPE)

There was constructed a calcium sensor having a dimethylamino group and having a maximum fluorescence wavelength of about 546 nm.

An acrylate monomer and a polymer each having a dimethylaminated TPE were synthesized as follows.

(1) A zinc powder (3.25 g) and 60 ml of tetrahydrofuran were placed in a reaction vessel under an argon gas atmosphere. The mixture was cooled to −5 to 0° C., and $TiCl_4$ (2.75 ml) was slowly added thereto by using a syringe maintained at 10° C. or lower. The mixture was stirred at room temperature for 0.5 hours, and refluxed under heating for 2.5 hours. The mixture was again cooled to −5 to 0° C., and pyridine (1.0 ml) was added and stirred for 10 min. A tetrahydrofuran (30 ml) solution of p-hydroxybenzophenone (0.99 g) and 4,4'-dimethylaminobenzophenone (1.34 g) was slowly added by using a syringe. After the addition, the reaction mixture was heated to 70° C., and refluxed until the raw materials disappeared on TLC. A 10% $K_2CO_3$ aqueous solution was added, and then, dichloromethane was added. An organic layer was washed with water and a saline solution, dried over $MgSO_4$, thereafter dried up under reduced pressure, and purified by silica gel column chromatography ($CHCl_3$:MeOH=95:5); and a product on the spot of an $R_f$ value of 0.30 was collected to thereby obtain a partially purified product (310 mg).

A dichloromethane (0.5 ml) solution of the partially purified product (43.4 mg) and triethylamine (56 μL) was cooled to 0° C., and a dichloromethane (5 ml) solution of acryloyl chloride (16 μL) was added dropwise. The reaction mixture was stirred at room temperature for 3 hours until the raw materials disappeared on TLC. Sodium hydrogen carbonate was added to the reaction liquid, and dichloromethane was further added. An organic layer was washed with water and a saline solution, dried over $MgSO_4$, and thereafter dried up under reduced pressure. The resultant was purified by silica gel column chromatography ($CHCl_3$:MeOH=99:1) to thereby obtain 42.7 mg of 4-hydroxy-4',4"-bis(dimethylamino)tetraphenylethylene acrylate (4',4"-bis(dimethylamino)TPE-acrylate) (two-stage yield: 12%).

$^1$H NMR (400 MHz, $CDCl_3$, 293 K) δ 7.03-7.26 (m, 7H), 6.87-6.91 (m, 6H), 6.56 (dd, J=17.29, 1.32 Hz, 1H), 6.47 (d, J=8.96 Hz, 2H), 6.45 (d, J=8.96 Hz, 2H), 6.28 (dd, J=17.29, 1.32 Hz, 1H), 5.96 (dd, J=10.44, 1.32 Hz, 1H), 2.90 (s, 6H), 2.88 (s, 6H) ppm $^{13}$C NMR (100 MHz, $CDCl_3$, 293 K) δ 164.4, 148.9, 148.9, 148.3, 145.0, 142.9, 141.7, 135.9, 132.5, 132.4, 132.2, 132.0, 131.6, 128.2, 127.6, 125.6, 120.4, 111.5, 111.4, 40.4 ppm.

FT-IR: ν 3449, 3083, 3035, 2921, 2889, 2802, 1746, 1608, 1519, 1444, 1402, 1354, 1294, 1248, 1198, 1166, 1153, 1126, 1065, 1018, 976, 946, 902, 818, 768, 739, 700, 589, 471, 454, 432, 420 $cm^{-1}$.

(2) A dimethylformamide (0.5 ml) solution of 4',4"-bis(dimethylamino)TPE-acrylate (12.2 mg, 5 mol %) obtained in (1), tert-butyl acrylate (69.0 μL, 95 mol %) and 2,2'-azobis(isobutyronitrile)(AIBN) was deoxygenated three times by using a reduced pressure/argon gas. The solution was stirred at 60° C. for 12 hours, and cooled to room temperature; and the solvent was distilled off to thereby obtain 73.0 mg of a (4',4"-bis(dimethylamino)TPE-acrylate)$_{0.05}$-(tert-butyl acrylate)$_{9.95}$-copolymer.

$^1$H NMR (400 MHz, $CDCl_3$, 293 K) δ 6.72-7.16 (m), 6.35-6.53 (m), 2.80-2.95 (m), 2.12-2.45 (m), 1.14-1.93 (m) ppm.

FT-IR (KBr) ν 3437, 2978, 2933, 1729, 1609, 1520, 1480, 1450, 1393, 1367, 1256, 1149, 947, 845, 752, 700, 578, 471, 449, 418 $cm^{-1}$.

$M_n$=24,000, $M_w$=44,000, PDI=1.86 (GPC: eluent; DMF, PSt standards).

(3) 30.0 mg of the copolymer obtained in (2) was dissolved in trifluoroacetic acid (400 μL), and stirred at room temperature for 12 hours. The solvent was distilled off from the reaction liquid to thereby obtain 17 mg of a (4',4"-bis(dimethylamino)TPE-acrylate)$_{0.05}$-(acrylic acid)$_{9.95}$-copolymer.

$^1$H NMR δ 6.83-7.21 (m), 3.01-3.24 (m), 2.31-2.60 (m), 1.45-2.18 (m) ppm

FT-IR (KBr) ν 3448, 2959, 1719, 1509, 1451, 1411, 1250, 1196, 1018, 901, 800, 723, 703, 605, 579, 521, 482, 443, 418 $cm^{-1}$ (4) When the copolymer obtained in (3) was dissolved in a mixed solvent of water/methanol=1/1 (10 mg/L), and calcium chloride was added dropwise, the fluorescence intensity increased and the copolymer functioned as a calcium sensor. The fluorescence spectrum had a maximum wavelength at 546 nm, and yellow emission was generated. It was thus found that, in this sensor, the emission wavelength could be selected by using an AIE pigment having a different emission wavelength.

Example 11 (Immobilization to a Base Material)

The polymer can also be immobilized on a base material by a surface-initiated polymerization (SIP) method. An immobilization method on a glass substrate will be described here. First, a RAFT agent capable of being immobilized on the substrate was prepared. Trimethoxysilylpropyl methacrylate (298 mg), 2-cyano-2-propyldodecyl trithiocarbonate (105 mg) and 2,2'-azobis(isobutyronitrile) (AIBN, 16 mg) were dissolved in a toluene (1.0 ml) solution, and deoxygenated three times using a reduced pressure/argon gas. The solution was stirred at 80° C. for 12 hours, and the solvent was distilled off under reduced pressure to thereby obtain the RAFT agent having a trimethoxysilyl group.

The glass substrate as an object of immobilization was well washed with sulfuric acid, hydrochloric acid and a UV ozone cleaner. The substrate was immersed in the toluene containing the RAFT agent having a trimethoxysilyl group of 0.01 mol/L, and allowed to stand at 80° C. for 16 hours. The system was returned to room temperature, and the substrate was taken out, washed with toluene, chloroform, dichloromethane, tetrahydrofuran, dimethylformamide, methanol and acetone, and dried under vacuum to thereby obtain a glass substrate having a RAFT initiation group immobilized thereon.

The modified glass substrate was immersed in a toluene (0.5 ml) solution of the TPE-acrylate (12.2 mg, 5 mol %), tert-butyl acrylate (69.0 µL, 95 mol %) and 2,2'-azobis (isobutyronitrile) (AIBN), and deoxygenated three times using a reduced pressure/argon gas. The system was stirred at 60° C. for 12 hours, and cooled to room temperature, and the substrate was washed with toluene, chloroform, dichloromethane, tetrahydrofuran, dimethylformamide, methanol and acetone to thereby obtain a glass substrate having a (TPE-acrylate)$_{0.05}$-(tert-butyl acrylate)$_{9.95}$-copolymer immobilized thereon. (ATR-FT-IR (Ge) ν 2979, 2935, 1729, 1481, 1457, 1393, 1367, 1258, 1149, 846, 752, 471 cm$^{-1}$) The substrate was immersed in trifluoroacetic acid, allowed to stand for 12 hours, and washed with toluene, chloroform, dichloromethane, tetrahydrofuran, dimethylformamide, methanol and acetone to thereby obtain a glass substrate having a (TPE-acrylate)$_{0.05}$-(acrylic acid)$_{9.95}$-copolymer immobilized thereon. (ATR-FT-IR (Ge) ν 2960, 1717, 1456, 1419, 1250, 1170, 802, 738 cm$^{-1}$) When the fluorescence spectrum of the glass substrate was measured, the emission derived from tetraphenylethene moieties was confirmed, and the immobilization to the base material was confirmed. The immobilization is allowed on any base material, as long as the base material is capable of being modified on its surface with a silane coupling agent.

Example 12

In addition to the SIP method, the polymer can be insolubilized also by gelation. A dimethylformamide (0.5 mM) solution of the TPE-acrylate (20.1 mg, 5 mol %), acrylic acid (61.7 µL, 90 mol %), tetraethylene glycol bisacrylate (15.1 mg, 5 mol %) and 2,2'-azobis(isobutyronitrile) (AIBN) was deoxygenated three times using a reduced pressure/argon gas. The solution was stirred at 60° C. for 12 hours to thereby obtain an insoluble solid. The solid was washed with dimethylformamide, tetrahydrofuran, methanol and acetone to thereby obtain a target gel. (FT-IR (KBr) ν 2934, 1729, 1645, 1444, 1388, 1254, 1167, 1106, 807, 702, 669 cm$^{-1}$)

The gel was immersed in a mixed solution of methanol/water=1/1, and when the fluorescence quantum yield was measured while calcium chloride was being added, it was found that as calcium chloride was added, the fluorescence quantum yield increased, and the gel functioned as a calcium sensor.

Example 13

The polymerization was carried out by replacing 1 mol % of AIBN by 2 mol % of 2,2-dimethoxy-1,2-diphenylethan-1-one (IRGACURE 651, BASF) as a photopolymerization initiator, and irradiating the system with white light. As a result, a similar gel as in Example 12 was obtained.

Example 14

Copolymers were obtained in a similar manner to Example 13 and by varying the ratio of the each monomer and carrying out the gelation polymerization. The relationship between structures, molar ratios and degrees of swelling of the obtained copolymers are shown in Table 2. Here, the degree of swelling represents a degree of swelling when a gel is swollen for 30 min using a mixed solvent of HEPES buffer (pH: 7.4)/methanol=1/1.

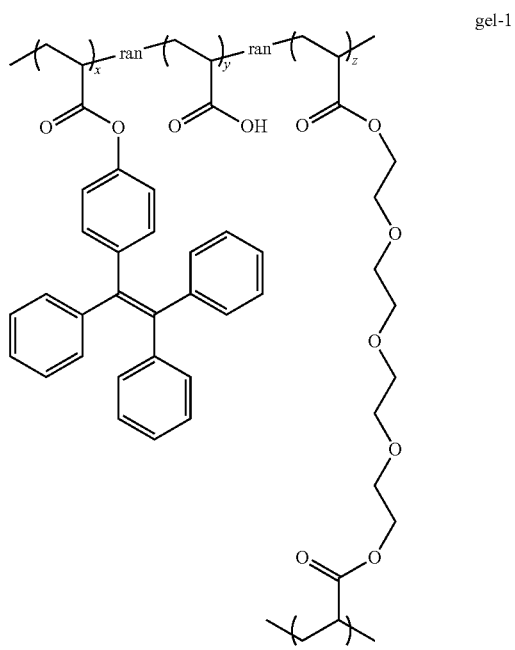

gel-1

TABLE 2

Degree of Swelling of gel-1 and Molar Ratio of z

| gel-1 | x | y | z | Degree of Swelling (%) |
|---|---|---|---|---|
| gel-1$_{0.001}$ | 5 | 94 | 1 | 2280 |
| gel-1$_{0.015}$ | 5 | 93.5 | 1.5 | 1600 |
| gel-1$_{0.02}$ | 5 | 93 | 2 | 2088 |
| gel-1$_{0.03}$ | 5 | 92 | 3 | 906 |
| gel-1$_{0.05}$ | 5 | 90 | 5 | 172 |
| gel-1$_{0.10}$ | 5 | 85 | 10 | 68 |

From Table 2, it is found that the degree of swelling varies depending on the molar ratio of z and the copolymer has been gelation-polymerized.

Example 15

(1) The Ca$^{2+}$ sensing capabilities of the copolymers obtained in Example 14 were evaluated. Ca$^{2+}$ was added to gel-1$_{0.01}$ to gel-1$_{0.10}$ swollen for 30 min in a mixed solvent of HEPES buffer/methanol=1/1, and the fluorescence quantum yields were measured in a similar manner to Example 7. The results are shown in FIG. 13.

From FIG. 13, it is found that when the molar ratio of z is 0.05 mol (5 mol %) or lower, the fluorescence quantum yield varies, and the measurement of Ca$^{2+}$ is possible.

(2) Then, the reversibility of gel-1 in the Ca$^{2+}$ sensing was studied. 0.2 mM of Ca$^{2+}$ was added to gel-1$_{0.03}$, gel-1$_{0.02}$, gel-1$_{0.015}$ and gel-1$_{0.01}$, and the fluorescence quantum yields were measured. Thereafter, the solvent was added and the Ca$^{2+}$ concentration was diluted to ½ (0.1 mM), and the fluorescence quantum yields were measured.

In gel-$1_{0.02}$, gel-$1_{0.015}$ and gel-$1_{0.01}$, whose crosslinking degrees were low, when the $Ca^{2+}$ concentration was diluted to 0.1 mM, the fluorescence quantum yields reduced and it was suggested that the $Ca^{2+}$ sensing was reversible. In gel-1 having a high degree of crosslinking, it is conceivable that when $Ca^{2+}$ was once incorporated, $Ca^{2+}$ was hardly released even if the concentration was diluted.

Then, by using gel-$1_{0.015}$, in order to obtain further knowledge on the reversibility, the change in the fluorescence quantum yield was measured by varying the $Ca^{2+}$ concentration repeatedly (FIG. 14). When the $Ca^{2+}$ concentration became high, the fluorescence quantum yield became high; and when the $Ca^{2+}$ concentration became low, the fluorescence quantum yield became low accompanying that; and the change was thus confirmed repeatedly. From this, it is conceivable that the $Ca^{2+}$ of gel-$1_{0.015}$ is reversible.

Example 16

The gelation polymerization was carried out in a similar manner to Example 12, by using AIBN (thermal polymerization initiator) as a polymerization initiator, and varying the molar ratio of the monomer (C) as a crosslinking agent. As a result, copolymers which gelated and were excellent in the $Ca^{2+}$ sensing capability were obtained, in the molar ratio range of the crosslinking agent of 1 to 5 mol % (z=0.01 to 0.05). Further, gels having a degree of swelling of 340% or higher, further of 340 to 1,500, and particularly of 500 to 1,500 were excellent in the $Ca^{2+}$ sensing capability.

Gels were synthesized by varying the polymerization concentration and the crosslinking agent addition amount (z) at this time (Table 3). All the gels were purified by washing the gels with methanol and acetone each for 12 hours using a Soxhlet extractor. Under the condition of z<1 in a polymerization concentration of 2.0 M, no gel was produced. The degrees of swelling (Table 3) of these gels after being swollen for 30 min in HEPES buffer (pH: 7.4)/methanol=1/1, and changes in the fluorescence quantum yields vs. the calcium addition (FIG. 15) were measured. The gels prepared in a polymerization concentration of 4.0 M exhibited a higher degree of swelling with z being lower, but any thereof was a low value. Further, even when calcium was added, the fluorescence quantum yields exhibited almost no change. In contrast, the gels prepared in a polymerization concentration of 2.0 M exhibited a remarkably higher degree of swelling with z being lower. Further, when calcium was added to these gels and the fluorescence quantum yields were measured, gel-1e and gel-1f exhibited almost no change in the fluorescence quantum yields, whereas gel-1g and gel-1h exhibited remarkably increased fluorescence quantum yields along with the addition of calcium. The gels prepared in a polymerization concentration of 1.5 M by diluting the polymerization concentration further low exhibited a higher degree of swelling. Further, when calcium was added to these gels and the fluorescence quantum yields were measured, in gel-1j, which had a higher degree of swelling, the fluorescence quantum yield remarkably increased along with the addition of calcium.

It is conceivable that since a gel having a higher degree of swelling has a higher mobility of polymer chains in the gel, a large change in the fluorescence quantum yield occurred.

TABLE 3

| gel-1 | Concentration at Polymerization | X | y | z | Degree of Swelling |
|---|---|---|---|---|---|
| gel-1a | 4.0M | 5 | 92 | 3 | 116% |
| gel-1b | 4.0M | 5 | 93.5 | 1.5 | 196% |
| gel-1c | 4.0M | 5 | 94 | 1 | 220% |
| gel-1d | 4.0M | 5 | 94.5 | 0.5 | 224% |
| gel-1e | 2.0M | 5 | 90 | 5 | 342% |
| gel-1f | 2.0M | 5 | 92 | 3 | 890% |
| gel-1g | 2.0M | 5 | 93.5 | 1.5 | 970% |
| gel-1h | 2.0M | 5 | 94 | 1 | 1150% |
| gel-1i | 1.5M | 5 | 90 | 5 | 780% |
| gel-1j | 1.5M | 5 | 92 | 3 | 1202% |

Example 17 (Calcium Sensing in Water)

Further, gel-1j exhibited the calcium sensing capability not only in HEPES buffer (pH: 7.4)/methanol=1/1 but also in HEPES buffer (pH: 7.4) (FIG. 16). Further, by decreasing the calcium concentration around the gel, the fluorescence quantum yield decreased to the initial value. After that, by increasing or decreasing the calcium concentration around the gel, the fluorescence quantum yield of the gel increased or decreased with good reproducibility (FIG. 17).

Example 18

(1) FIG. 18 shows a conceptual view of constructing a flexible sensor by combining a $Ca^{2+}$ sensing gel with an OLED and an OPV on a flexible substrate.

(2) Construction of a sensor having a different absorption wavelength and fluorescence wavelength When such a combination with an OLED and an OPV is made, it is important to adjust the wavelengths of the excitation light and the fluorescence. In such a case, the adjustments can be made by varying the chemical structure of fluorescent sites.

For example, a derivative in which two dimethylamino groups are incorporated to tetraphenylethene has absorption and fluorescence at a longer wavelength side than non-substituted tetraphenylethene. Then, the present inventors synthesized monomer 1-$NMe_2$ in which a vinyl group was incorporated in tetraphenylethene having dimethylamino groups.

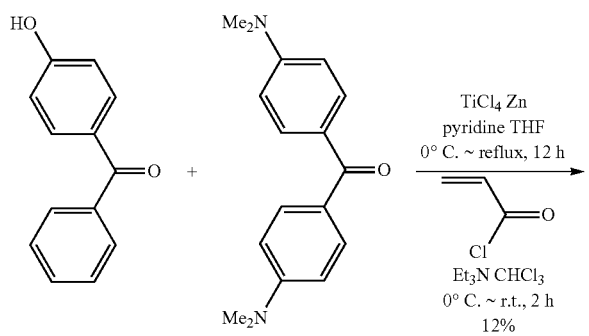

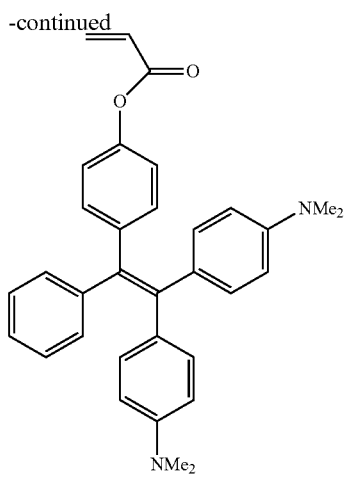

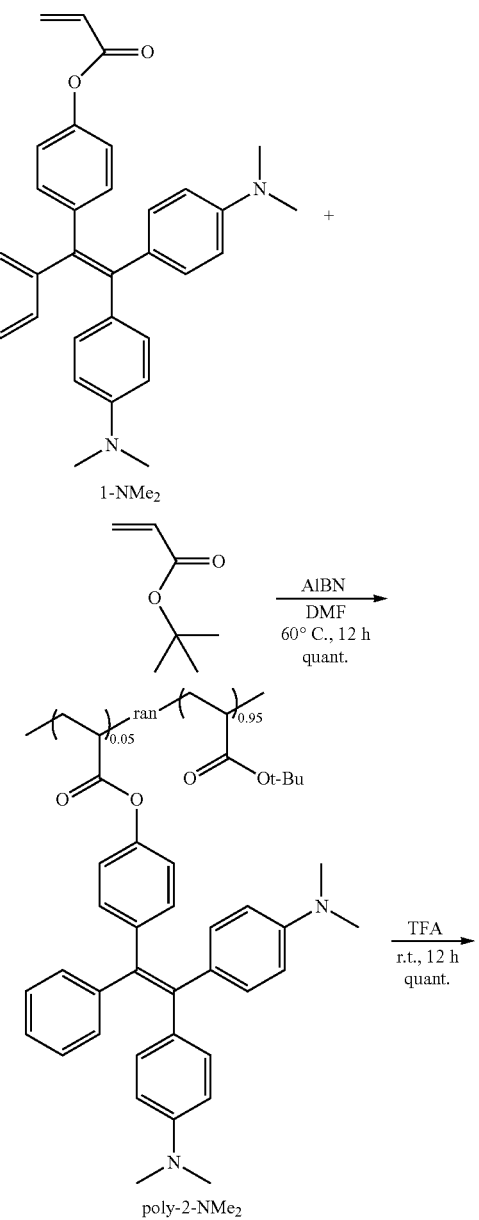

(3) A zinc powder (3.25 g) and 60 ml of tetrahydrofuran were placed in a reaction vessel under an argon gas atmosphere. The mixture was cooled to −5 to 0° C., and TiCl$_4$ (2.75 ml) was slowly added by using a syringe maintained at 10° C. or lower. The mixture was stirred at room temperature for 0.5 hours, and refluxed under heating for 2.5 hours. The mixture was again cooled to −5 to 0° C., and pyridine (1.0 ml) was added and stirred for 10 min. A tetrahydrofuran (30 ml) solution of p-hydroxybenzophenone (0.99 g) and dimethylaminobenzophenone (1.34 g) was slowly added by using a syringe. After the addition, the reaction mixture was heated to 70° C., and refluxed until the raw materials disappeared on TLC. A 10% K$_2$CO$_3$ aqueous solution was added, and then, dichloromethane was added. An organic layer was washed with water and a saline solution, dried over MgSO$_4$, thereafter dried up under reduced pressure, and purified by silica gel column chromatography (CH$_2$Cl$_2$:MeOH=95:5) to thereby obtain 310 mg (yield: 14%) of p-hydroxydimethylaminotetraphenylethylene.

A dichloromethane (500 μL) solution of the p-hydroxydimethylaminotetraphenyl ethylene (43.4 mg) and triethylamine (56.0 μL) was cooled to 0° C., and a dichloromethane (500 μL) solution of acryloyl chloride (16.0 μL) was added dropwise. The reaction mixture was stirred at room temperature for 2 hours until the raw materials disappeared on TLC. Sodium hydrogen carbonate was added to the reaction liquid, and dichloromethane was further added. An organic layer was washed with water and a saline solution, dried over MgSO$_4$, thereafter dried up under reduced pressure, and purified by silica gel chromatography (CHCl$_3$:MeOH=99:1) to thereby obtain 42.7 mg (yield: 88%) of p-hydroxytetradimethylaminophenylethylene acrylate, which is abbreviated to 1-NMe$_2$ hereinafter.

Yellow solid: $^1$H NMR (400 MHz, CDCl$_3$) δ 7.00-7.15 (m, 7H), 6.85-6.93 (m, 6H), 6.56 (dd, J=17.0, 1.3 Hz, 1H), 6.46 (t, J=8.7 Hz, 4H), 6.27 (dd, J=10.5, 17.3 Hz, 1H), 5.99 (dd, J=10.5, 1.3 Hz, 1H), 2.89 (d, J=4.9 Hz, 12H) ppm.

FT-IR (KBr) ν 3469, 3034, 2886, 2801, 1747, 1608, 1520, 1444, 1403, 1354, 1294, 1249, 1167, 1065, 1017, 977, 947, 903, 819, 768, 740, 702, 580, 538 cm$^{-1}$.

HRMS(FAB) Calcd for C33H32N2O2 [M]+ m/z=488.2464. Found: m/z=488.2470.

(4) Then, a polyacrylic acid (poly-1-NMe$_2$) having a dimethylaminated tetraphenylethene as a fluorescent site was synthesized by polymerizing 1-NMe$_2$ in a similar manner to Example 2(1) and (2).

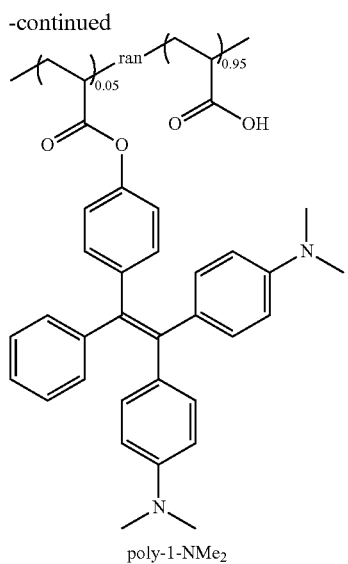

poly-1-NMe₂ poly-2-NMe₂

Yellow solid: ¹H NMR (400 MHz, CDCl₃) δ 6.72-7.15, 6.38-6.56, 2.79-2.92, 2.09-2.50, 2.34-2.98 ppm.

FT-IR (KBr) ν 3437, 2979, 2933, 1730, 1609, 1521, 1480, 1450, 1393, 1367, 1256, 1149, 846, 752, 700, 472 cm⁻¹.

poly-1-NMe₂

Yellow solid: ¹H NMR (400 MHz, CDCl₃) δ 6.79-7.37, 2.28-2.57, 1.36-2.14 ppm.

FT-IR (KBr) ν 3448, 2959, 1719, 1509, 1451, 1411, 1251, 1197, 800, 723, 704 cm⁻¹.

(5) The obtained poly-1-NMe₂ exhibited absorption and fluorescence on a longer wavelength side than poly-1 (FIG. 19). Further, when CaCl₂ was added to this solution, the fluorescence intensity increased and the poly-1-NMe₂ also functions as a calcium sensor (FIG. 20).

From these results, it is found that by changing the structure of AIE sites, the absorption wavelength (excitation wavelength) and the fluorescence wavelength (detection wavelength) can be varied, and calcium sensors compatible with various types of OLED and OPV can be designed.

The invention claimed is:

1. A copolymer, comprising a repeating unit (A) comprising a carboxyl group on a side chain thereof, and a repeating unit (B) comprising a carboxylate group having an ester residue exhibiting an aggregation-induced emission capability on a side chain thereof,
   wherein the repeating unit (A) is a repeating unit derived from a monomer selected from the group consisting of acrylic acid, methacrylic acid and styrenecarboxylic acid;
   wherein the repeating unit (B) is a repeating unit derived from at least one monomer selected from the group consisting of an acrylate, a methacrylate and a styrenecarboxylate; and
   wherein the ester residue is derived from 1-methyl-1,2,3,4,5-pentaphenylsilole, 2,3,4,5-tetraphenyl-1,1-dimethylsilole or tetraphenylethylene, each of which optionally have 1 to 5 hydrophilic groups substituted on a phenyl group thereof, wherein the hydrophilic groups are independently selected from the group consisting of hydroxy group, an amino group, an alkylamino group, a dialkylamino group, a thiol group, a polyoxyethylene group, a polyoxypropylene group and a sulfinyl group.

2. The copolymer according to claim 1, wherein the copolymer has a molar ratio of the repeating unit (A) to the repeating unit (B), (A:B) 4:1 to 1000:1.

3. The copolymer according to claim 1, wherein the copolymer has a number-average molecular weight of 10,000 to 1,000,000.

4. The copolymer according to claim 1, wherein the copolymer is a copolymer adapted to function as a polymer for detecting polyvalent metal ion fluorescence.

5. The copolymer according to claim 1, further comprising a repeating unit (C) derived from a polyfunctional monomer.

6. The copolymer according to claim 5, wherein the copolymer comprises 0.1 to 10 mol % of the repeating unit (C).

7. The copolymer according to claim 5, wherein the repeating unit (C) is a repeating unit derived from a monomer having two or more polymerizable vinyl groups.

8. A device for detecting a polyvalent metal ion, the device comprising the copolymer according to claim 1.

9. The device of claim 8, wherein the copolymer is immobilized on a solid base material.

10. The device of claim 9, wherein the copolymer is immobilized on the solid base material by covalent bonding to the solid base material.

11. A method for quantifying a polyvalent metal ion concentration in a sample, the method comprising contacting the sample with the device of claim 8, and measuring a fluorescence intensity.

12. The copolymer according to claim 1, wherein the hydrophilic groups are independently selected from a $C_1$ to $C_6$ alkylamino group and a di($C_1$ to $C_6$ alkyl)amino group.

13. The copolymer according to claim 1, wherein the ester residue is derived from 1-methyl-1,2,3,4,5-pentaphenylsilole.

14. The copolymer according to claim 1, wherein the ester residue is derived from 2,3,4,5-tetraphenyl-1,1-dimethylsilole.

15. The copolymer according to claim 1, wherein the ester residue is derived from tetraphenylethylene optionally having 1 to 5 hydrophilic groups substituted on a phenyl group thereof, wherein the hydrophilic groups are independently selected from the group consisting of hydroxy group, an amino group, an alkylamino group, a dialkylamino group, a thiol group, a polyoxyethylene group, a polyoxypropylene group and a sulfinyl group.

16. The copolymer according to claim 1, wherein a carboxyl group in the repeating unit (A) on a side chain is a hydrophilic group having bonding site that can bind to the target polyvalent metal ions.

17. The copolymer according to claim 1, wherein the repeating unit (A) is acrylic acid.

18. The copolymer according to claim 1, wherein the repeating unit (A) is methacrylic acid.

19. The copolymer according to claim 1, wherein the repeating unit (A) is styrenecarboxylic acid.

* * * * *